United States Patent [19]
Eiden et al.

[11] Patent Number: 6,033,905
[45] Date of Patent: Mar. 7, 2000

[54] GIBBON APE LEUKEMIA VIRUS-BASED RETROVIRAL VECTORS

[75] Inventors: Maribeth V. Eiden, Bethesda, Md.; Carolyn A. Wilson, Arlington, Va.; Nicholas J. Deacon, Balwyn; David J. Hooker, Mill Park, both of Australia

[73] Assignee: The United States of America as represented by the Department of Health and Human Services, Washington, D.C.

[21] Appl. No.: 08/716,351

[22] PCT Filed: Apr. 6, 1994

[86] PCT No.: PCT/US94/03784

§ 371 Date: Feb. 24, 1997

§ 102(e) Date: Feb. 24, 1997

[87] PCT Pub. No.: WO94/23048

PCT Pub. Date: Oct. 13, 1994

Related U.S. Application Data

[63] Continuation of application No. 08/043,311, Apr. 6, 1993, abandoned.

[51] Int. Cl.[7] ............................... C12N 15/00; C12N 5/00
[52] U.S. Cl. ...................... 435/320.1; 435/325; 435/440; 435/455; 435/456
[58] Field of Search .............................. 435/235.1, 320.1, 435/325, 172.3, 440, 455, 456; 424/93.1, 93.2, 93.21; 514/44

[56] References Cited

U.S. PATENT DOCUMENTS 5,470,726 11/1995 Miller et al. ......................... 435/172.3

OTHER PUBLICATIONS

Wilson et al. Development of a novel MoMLV–based vector system with the host range of a type C primate retrovirus. J. Cell Biochem., Suppl. 0 (12 Part C), p. 48, 1988.

Houdebine L. M. Production of pharmaceutical proteins from transgenic animals. J. of Biotech., vol. 34, pp. 269–287, 1994.

Orkin et al. Report and recommendations of the panel to assess the NIH investment in research on gene therapy. Distributed by the National Institutes of Health, Bethesda, MD., Dec. 7, 1995.

Wilson et al. Formation of Infectious hybrid virions with Gibbon Ape Leukemia Virus and Human T–Cell Leukemia Virus Retroviral envelope glycoproteins and the gag and pol proteins of Moloney murine Leukemia Virus. J. of Virol., vol. 63, No. 5, p. 2374, May 1989.

*Primary Examiner*—Deborah Crouch
*Assistant Examiner*—Deborah J. R. Clark
*Attorney, Agent, or Firm*—Townsend and Townsend and Crew

[57] ABSTRACT

The present invention provides replication-defective hybrid retroviral vectors comprising GaLV components and methods for preparing and using such vectors. The vectors comprise a envelope component, a core component and a defective genome, at least one of which is derived from GaLV. The vectors can comprise the minimal cis acting sequences from GaLV that allow packaging of the defective genome in a hybrid virion.

22 Claims, 9 Drawing Sheets

STEP

7

8

INTERMEDIATE CLONE 120

INTERMEDIATE CLONE 66

STEP

COMPLETE Not I SITE
——— GCGGCCGC ———
——— CGCCGGCG ———

INTERMEDIATE CLONE 120Exo55

STEP 33-37

38

CLONE II
= pGaLV-II

GIBBON APE LEUKEMIA VIRUS-BASED RETROVIRAL VECTORS

CROSS-REFERENCE TO RELATED APPLICATIONS

This application claims priority under 35 U.S.C. § 371 to PCT/US94/03784, filed Apr. 6, 1994, which is a continuation of U.S. Ser. No. 08/043,311, filed Apr. 6, 1993 abandoned; both of which are herein incorporated by reference in their entirety.

FEDERALLY SPONSORED RESEARCH AND DEVELOPMENT

Not applicable.

BACKGROUND OF THE INVENTION

The present invention relates generally to retroviral vectors. In particular, the invention relates to retroviral vectors comprising nucleic acid sequences from Gibbon Ape Leukemia Virus.

Considerable effort is now being directed to introducing engineered genes into mammalian cells for a variety of applications including gene therapy and the production of transgenic animals. Such strategies are dependent upon the development of effective means for safe delivery of genes to appropriate target cells and tissues.

Retroviral vectors are particularly useful for directing desired polynucleotides to the appropriate cells and integration of the polynucleotides in the host cell genome. For example, the majority of the approved gene transfer trials in the United States rely on replication-defective retroviral vectors harboring a therapeutic polynucleotide sequence as part of the retroviral genome (Miller et al. *Mol. Cell. Biol.* 10:4239 (1990); Kolberg R *J. NIH Res.* 4:43 (1992); Cornetta et al. *Hum. Gene Ther.* 2:215 (1991)). As is known in the art, the major advantages of retroviral vectors for gene therapy are the high efficiency of gene transfer into certain types of replicating cells, the precise integration of the transferred genes into cellular DNA, and the lack of further spread of the sequences after gene transfer.

Unfortunately, many human cells are not efficiently infected by prior art retroviral vectors. Reduced susceptibility to retroviral infection is most likely due to inefficiencies in one of three stages of viral replication: 1) binding to retroviral receptors on the cell surface and early viral entry, 2) late entry and transport of the viral genome to the cell nucleus and integration of the viral genome into the target cell DNA, and 3) expression of the viral genome. These three stages are governed, respectively, by the viral envelope proteins, the viral core proteins, and the viral genome. All three of these components must function efficiently in a target cell to achieve optimal therapeutic gene delivery.

Gibbon Ape Leukemia Virus (GaLV) uses a cell surface internalization receptor that is different from those of the available retroviral vectors and thus allows infection of cells and tissues normally resistant to retroviral infection. The human receptor for GaLV has recently been cloned and shows a wide cell type and species distribution. Johann et al., *J. Virol.* 66:1635–1640 (1992). Indeed, GaLV can infect many mammalian species with the notable exception of mouse cells. The same receptor is used by simian sarcoma associated virus (SSAV), a strain of GaLV. Sommerfelt et al., *Virol.* 176:58–59 (1990).

The construction of hybrid virions having GaLV envelope proteins has been demonstrated. For instance, Wilson et al., *J. Virol.* 63:2374–2378 (1989), describe preparation of infectious hybrid virions with GaLV and human T-cell leukemia virus retroviral env glycoproteins and the gag and pol proteins of the Moloney murine leukemia virus (MoMLV). In addition, Miller et al., *J. Virol.* 65:2220–2224 (1991), describe construction of hybrid packaging cell lines that express GaLV envelope and MoMLV gag-pol proteins.

Existent retroviral vectors capable of infecting human cells all contain core and genome components that derive from MoMLV. For human cells which are resistant to efficient infection by such vectors at any of the three stages noted above, new vectors comprising improved envelope, core or regulatory sequences must be designed. Thus, there is a need to design retroviral vectors components which can be used to introduce genes into human cells not efficiently infected by the currently utilized retroviral vectors. The present invention addresses these and other needs.

SUMMARY OF THE INVENTION

The present invention provides recombinant DNA constructs comprising a defective viral genome having a polynucleotide sequence of interest and a GaLV component. For instance, the GaLV component may be a GaLV packaging site which directs packaging of the defective viral genome in an infectious, replication-defective virion. The packaging site typically consists of between about 150 base pairs and about 1500 base pairs and includes a sequence extending from about position 200 to about position 1290 of the sequence shown in SEQ ID NO.:1.

The construct may further comprise GaLV regulatory sequences which direct expression of the polynucleotide of interest. Typically, the regulatory sequences comprise a GaLV (e.g., GaLV SEATO or GaLV SF) 5' or 3' LTR promoter.

The invention also relates to mammalian cells comprising the defective viral genome described above. The mammalian cells may be packaging cells, in which case the cells will also contain retroviral gag, pol and env genes. These genes may be derived from MoMLV, GaLV SF or GaLV SEATO. Packaging cells conveniently used in the invention include PG13 and PA317.

The invention further provides isolated hybrid virions comprising GaLV (e.g., SF or SEATO) envelope proteins and an RNA genome comprising a polynucleotide sequence of interest and a GaLV component. The virions typically contain GaLV core proteins. MoMLV core proteins can also be used.

The invention also provides isolated recombinant DNA constructs comprising polynucleotide sequences which encode an infectious GaLV virion capable of infecting a mammalian cell and producing functional viral progeny. The infectious clones typically comprise about 97% GaLV SEATO sequences and 3% GaLV SF sequences.

Also disclosed are methods of introducing a polynucleotide of interest into human cells using the hybrid virions described above. The methods are preferably used as part of a gene therapy protocol for treating a human patient.

DEFINITIONS

A "hybrid virion" is a virion comprising genome, core, and envelope components derived from more than one virus. The term specifically includes "pseudovirions" which historically have been defined as containing the genome from one virus and the structural proteins from another.

A "packaging cell" is a genetically constructed mammalian tissue culture cell that produces the necessary viral structural proteins required for packaging. The cells are incapable of producing infectious virions until a defective genome is introduced into the cells. The genetic material for the viral structural proteins is not transferred with the virions produced by the cells, hence the virus cannot replicate.

A "replication-defective" virion or retroviral vector is one produced by a packaging cell as defined above. Such a virion infects a target cell but is incapable of producing progeny virions which can infect other cells.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. These references are incorporated herein by reference.

The percentage of sequence identity between two sequences is determined by comparing two optimally aligned sequences over a window of comparison of at least 20 positions. The percentage is calculated by determining the number of positions at which the identical nucleic acid base or amino acid residue occurs in both sequences to yield the number of matched positions, dividing the number of matched positions by the total number of positions in the window of comparison (i.e., the window size), and multiplying the result by 100 to yield the percentage of sequence identity.

For instance, a preferred method for comparing sequences uses the GAP program based on the algorithm of Needleman at al., supra. Typically, the default values for all parameters are selected. These are gap weight: 5.0, length weight: 0.30, average match: 1.0, and average mismatch: 0.0.

The term "substantial identity" means that a polynucleotide or polypeptide comprises a sequence that has at least 80% sequence identity, preferably 90%, more preferably 95% or more, compared to a reference sequence over a comparison window of about 20 bp to about 2000 bp, typically about 50 to about 1500 bp, usually about 350 bp to about 1200. The values of percent identity are determined using the GAP program, above.

Another indication that nucleotide sequences are substantially identical is if two molecules hybridize to each other under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 60° C.

DESCRIPTION OF THE PREFERRED EMBODIMENTS

Figure 1A:
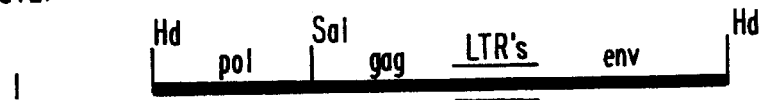
FIGS. 1A–1F show the construction of the infectious GaLV clone of the invention.
Figure 1A:
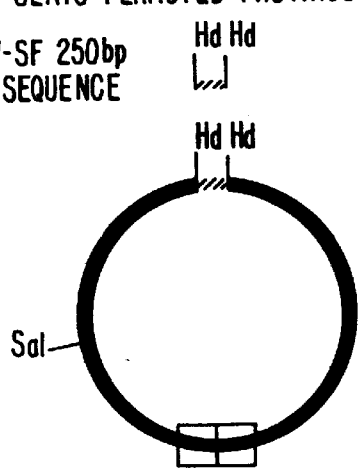
Figure 1A:
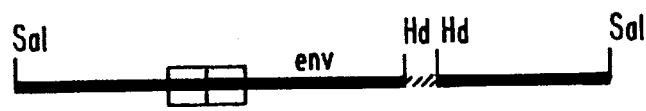
Figure 1A:
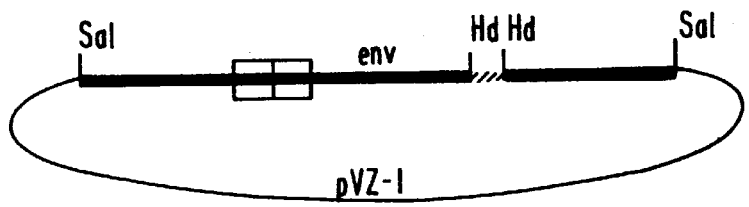
Figure 1A:
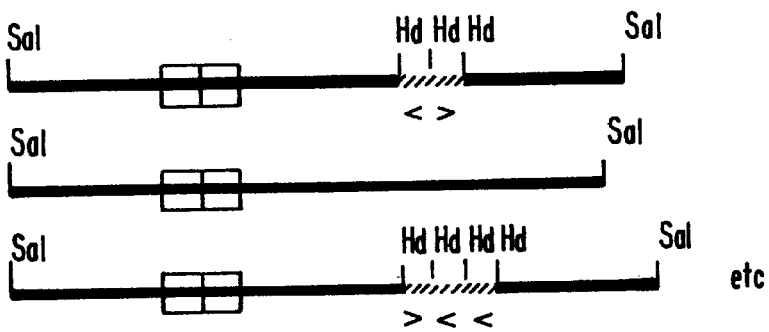

New hybrid retroviral vectors comprising GaLV components are provided by the present invention. The tissue specificity of the vectors is determined by the viral envelope proteins, the viral core proteins, and the viral genome, at least one of which is derived from GaLV. The vectors can comprise the minimal cis acting sequences (packaging signals) from GaLV that allow packaging of a defective genome in a replication-defective hybrid virion. In addition, the LTR of the defective genome can be derived from GaLV. For instance, the 3' LTR region of the hybrid retroviral vector can be selected from various GaLV sequences to provide desired tissue specific expression of the structural genes in the genome.

Replication-defective retroviral vectors are produced when a defective DNA viral genome is introduced into a packaging cell line. The defective genome contains the sequences required for integration into the target cell genome, for packaging of the genome into infectious virions, as well as those viral sequences required for expression of the therapeutic gene or other polynucleotide contained within the defective viral genome. The packaging cells comprise the gag, pol, and env genes which encode the viral core and envelope components. These core and envelope proteins assemble around the defective genome, thus producing retroviral vectors.

A number of standard techniques are used to ensure safety of retroviral vectors. For instance, the defective genome is introduced into the cell separately from the genes encoding the core and envelope components. In this way, recombination between the genome and the core and envelope genes, which would lead to the packaging of complete viral genomes, is extremely unlikely. The resulting virions should therefore not comprise the gag, pol, and env genes and are thus replication-defective. Homologous recombination, however, between the inserts can lead to the production of infectious virions. Typically, the packaging cells are produced by introducing the gag, pol, and env genes on at least two separate plasmids. This scheme effectively prevents homologous recombination leading to reconstruction of infectious virus because the probability of multiple, independent homologous recombination events occurring is extremely low.

Retroviral vectors can also be designed to prevent synthesis of viral proteins by the integrated defective genome. For instance, if a portion of the gag gene is included to increase packaging efficiency, a stop codon can be introduced into the gene to prevent synthesis of gag proteins. Miller et al., *BioTechniques* 7:982–988 (1989), which is incorporated herein by reference.

In addition, the cells used to make packaging cells do not possess a cell receptor for GaLV and are thus not infectable by GaLV. Retroviral vector virions having the GaLV envelope therefore cannot reinfect the packaging cells and vector spread in the packaging cells is greatly reduced. Suitable packaging cells also have limited or no endogenous viral sequences. Cell lines for this purpose include the Mus dunni tail fibroblast cell line. This strategy decreases the potential for generation of recombinant vectors, which are often transmitted with higher efficiency than the parental vector.

Finally, replication-defective vectors of the invention are particularly safe because GaLV is evolutionarily derived from a xenotropic virus of an asian strain of mouse and does not appear to be closely related to human pathogenic viruses. Thus, in terms of containment, GaLV-based, replication-defective hybrid virions are as safe as prior art murine retroviral vectors and provide a safe vehicle for delivery of genes for human gene therapy.

The packaging cell lines of the invention can be used to provide infectious replication-defective hybrid virions for use in gene transfer in humans, hamsters, cows, cats, dogs, monkeys, chimpanzees, macaques, primates, and other species whose cells have host cell receptors for GaLV envelope proteins.

Generally, the nomenclature used hereafter and the laboratory procedures in cell culture, molecular genetics, and nucleic acid chemistry described below are those well known and commonly employed in the art. Standard techniques are used for recombinant nucleic acid methods, polynucleotide synthesis, and cell culture. Generally, enzymatic reactions, oligonucleotide synthesis, oligonucleotide modification, and purification steps are performed according to the manufacturers' specifications. The techniques and procedures are generally performed according to conventional methods in the art and various general references which are provided throughout this document. A basic text disclosing the general methods of use in this invention is Sambrook et al., *Molecular Cloning, A Laboratory Manual*, Cold Spring Harbor Publish., Cold Spring Harbor, N.Y. 2nd ed. (1989), which is incorporated herein by reference.

A first step in the synthesis of retroviral vectors of the invention is obtaining an infectious GaLV DNA clone. Proviral DNA from at least three GaLV strains (GaLV SF, GaLV SEATO, and SSAV) has been cloned. A GaLV SF clone including both ends of the GaLV SF genome and the envelope gene but not an intact region of the genome encoding the core proteins is reported by Scott et al. *Proc. Natl. Acad. Sci. USA* 78:4213–4217 (1981). A partial clone containing the envelope and part of the genome but not the region encoding core proteins of SSAV is described by Gelman et al. *Proc. Natl. Acad. Sci. USA* 78:3373–3377 (1981). Finally, Gelman et al. *J. Virol.* 44:269–275 (1982) disclose a partial clone of a third GaLV strain, SEATO, containing all but 350 bases of the core region of GaLV. This clone has been sequenced in its entirety by Delassus et al. *Virol.* 173:205–213 (1989) (see FIG. 1). The deleted 350 bases were also sequenced but from a PCR fragment generated from viral RNA expressed in a GaLV SF infected cell line. The sequence of an integrated form of a GaLV SEATO genome is also shown in Seq ID No. 1. All of the above references are incorporated herein by reference.

Example 1 describes the construction of an infectious GaLV clone comprising sequences from GaLV SEATO and GaLV SF. This construction can be used to prepare a number of retroviral vectors, as described in detail below.

Packaging Cells

Packaging cells for use in the present invention may be made from any animal cell, such as CHO cells, NIH 3T3, mink lung cells, D17 canine cells, and MDBK cells. One or both of the core and envelope components can be encoded by GaLV genes. The core and envelope components, however, need not be derived from the same GaLV strain. Indeed, in some embodiments, the core components may be derived from a different species (e.g. MoMLV). For example, the PG13 murine packaging cell line produces virion particles having MoMLV core and GaLV envelope particles (see Miller, et al. (1991) *J. Virol.* 65:2220–2224).

To prepare a packaging cell line, an infectious clone of a desired retrovirus (e.g., GaLV SEATO) in which the packaging site ($\psi$) has been deleted is constructed. Cells comprising this construct will express all GaLV structural proteins but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

Although certain cells may express the receptor for a retroviral vector, the cells may not be efficiently infected because of a loss of optimum fit between the receptor and the envelope proteins. For example, altered glycosylation patterns may inhibit retroviral infection (Wilson et al., *J. Virol.* 65:5975–5982 (1991), which is incorporated herein by reference). In addition, retroviruses in the same receptor class can exhibit different host ranges due to single amino acid differences in target cell receptors.

In light of these considerations, it may be necessary to modify the envelope proteins of the hybrid virions to adjust the host range. The proteins may be modified to either allow infection of cells previously resistant to infection or to prevent infection of non-target cells.

One strategy for modifying envelope proteins is the use of an in vitro selection scheme. In this approach, an infectious clone of the retrovirus along with a selectable marker gene is introduced into target cells that are resistant to infection. Those cells which have been infected by retroviruses comprising mutations allowing infection of the cells are then identified by standard reverse transcriptase assays of the culture supernatant. The env gene of the adapted retrovirus is cloned and sequenced and used to construct new retroviral vectors capable of efficiently infecting the target cell. This strategy is particularly useful in isolating variants capable of infecting a number of human cells currently resistant to GaLV infection such as tumor infiltrating lymphocytes, bone marrow cells, stem cells, and hepatocytes.

Alternatively, if the gene encoding the cell receptor has been cloned, the gene can be inserted in a cell line which does not normally produce the receptor. Variant retroviruses capable of binding the receptor can then be identified in the same manner as described above. For instance, the human GaLV cell surface receptor has been cloned and sequenced. U.S. Pat. No. 5,151,361, and Johann et al., *J. Virol.* 66:1635–1640 (1992), which are incorporated herein by reference. Thus, this gene can be used to identify new retroviral vectors expressing modified envelope proteins.

A third alternative to modifying the host range of a retrovirus vector is by directly modifying the envelope proteins. Modifications of the sequences encoding the polypeptides may be readily accomplished by a variety of well-known techniques, such as site-directed mutagenesis (see, e.g., Gillman and Smith, *Gene* 8:81–97, (1979) and Roberts, S. et al., *Nature* 328:731–734, (1987), which are incorporated herein by reference). The effect of the modifications are evaluated by screening for the ability of the engineered virions to infect a target cell.

In addition, specific polynucleotide sequences encoding desired polypeptides can be fused to the env gene using methods known to those skilled in the art. Gene fusions comprising sequences encoding antibodies, SCF, IL-6 somatostatin and the like can thus be used as a targeting means. The fused gene can be inserted into an appropriate plasmid for transformation into the packaging cells.

In addition, the envelope protein can be modified for example, by introducing point mutations in the protein to yield moieties for coupling by organic chemical means (e.g., insertion of a cysteine residue to give a sulfhydryl group). Cell-specific targeting moieties can be coupled with glutaraldehyde, periodate, or maleimide compounds, or by other means known to those skilled in the art. Such couplings may also be made directly to wild-type or unmodified envelope proteins where coupling can be to a carbohydrate moiety, a sulfhydryl group, an amino group, or other group which may be available for binding.

A number of packaging cell lines suitable for the present invention are also available in the prior art. These lines include Crip and GPE-Am. Preferred existing cell lines include PA317 (ATCC CRL 9078) which expresses MoMLV core and envelope proteins and PG13 (ATCC CRL 10,683) which produces virions having MoMLV core and GaLV envelope components. (See Miller et al. *J. Virol.* 65:2220–2224 (1991), which is incorporated herein by reference.) The PG13 packaging cell line can be used in conjunction with the 521 plasmid and the 537 plasmid, both of which contain 5' MoMLV LTR and packaging signal sequences (see Example 3, herein).

Defective Genomes

The other component of retroviral vectors is a packagable defective genome comprising a polynucleotide sequence, typically a structural gene, of interest. The defective genomes of the invention include a GaLV component which include minimal GaLV nucleotide sequences must be present in the defective genome itself for the genome to integrate in the target cell genome and be packaged in infectious virions (i.e. the sequences are required in cis). Thus, the GaLV component of the defective genomes of the invention may include the packaging site, ψ, and/or the long terminal repeated sequences (LTRs). The LTRs are positioned at either end of the proviral DNA and contain regulatory sequences (e.g., promoters, enhancers and polyadenylation sequences) which direct expression of the genes within the proviral DNA. The polynucleotide sequences of the GaLV component may be identical to sequences as shown, for instance, in SEQ ID. No 1, or may be substantially identical to that sequence as defined, above.

Typically, the proviral regulatory sequences drive expression of the inserted gene. In those embodiments where two inserted genes are included (e.g., a marker gene and the gene of interest) it is frequently desirable to include a virus internal ribosome entry site (IRES) to increase efficiency of expression (Ghattas et al., *Mol. Cell. Biol.* 11:5848–5859 (1991), which is incorporated herein by reference).

The promoter operably linked to the gene of interest may be constitutive, cell type-specific, stage-specific, and/or modulatable (e.g., by hormones such as glucocorticoids). Suitable promoters for the invention include those derived from genes such as early SV40, CMV major late, adenovirus immediate early, histone H4, β-actin, MMTV, and HSV-TIC.

Enhancers increase the rate of transcription from promoters, act on cis-linked promoters at great distances, are orientation independent, and can be located both upstream, (5'), and downstream, (3'), from the transcription unit. Enhancers inducible by hormones and metal ions and found only in specific tissues have been described. Proteins synthesized only in one tissue type, for example, actin and myosin in muscle, are frequently regulated by tissue specific enhancers. For tissue specific expression of the introduced genes of interest used in the retroviral vectors of the present invention, tissue-specific enhancers are of particular interest.

A repetitive 45 base pair enhancer element in the U3 region of the GaLV LTR is important for tissue specific expression of the introduced genes. This enhancer region is present only once in the 3' LTR of GaLV SF but is present 3 times in the 3' LTR of GaLV SEATO. (See Quinn et al., *Mol. Cell. Biol.* 7:2735–2744, which is incorporated herein by reference). The sequence of the 3' LTR of GaLV SEATO with 3 repeats of the 45 bp enhancer region is shown in Seq. ID No.2. Thus, the origin of the 3' GaLV LTR region (from GaLV SEATO or GaLV SF) in a retroviral vector can influence the expression of the introduced gene in different tissues (see Example 4, herein).

To ensure efficient expression, 3' polyadenylation regions must be present to provide for proper maturation of the mRNA transcripts. The native 3'-untranslated region of the gene of interest is preferably used, but the polyadenylation signal from, for example, SV40, particularly including a splice site, which provides for more efficient expression, could also be used. Alternatively, the 3'-untranslated region derived from a gene highly expressed in a particular cell type could be fused with the gene of interest.

The retroviral vectors of the invention also contain GaLV-based regulatory elements that can direct expression of genes contained within the genome in a tissue/cell specific manner. In general, the GaLV regulatory elements are more efficient than the MoMLV elements in expressing genes in human cells. In addition, the regulatory sequences from different GaLV strains have different cell and tissue specificities. For instance, GaLV SF regulatory genes function efficiently in primate lymphoid cells (e.g., UCD 144) and GaLV SEATO regulatory genes function efficiently in human myeloid cells (e.g., HL60 cells), while MoMLV regulatory genes do not. Thus, tissue specificity of the vectors of the invention can be modified by selecting the appropriate GaLV strain. Tissue specificity of the regulatory genes from various GaLV strains is determined using routine screening techniques well-known to those of skill in the art.

The 5' and 3' LTRs of one retrovirus or GaLV strain may be also used in a defective genome derived from another. For instance, the 3' LTR from SSAV can be substituted for the 3' LTR of an infectious clone of another GaLV strain. Since the U3 region of the 3' LTR is the template for the synthesis of the U3 region in both 5' and 3' LTRs of the progeny virus, the 3' LTR will be duplicated and transferred to the 5' LTR in the host cell. In this way optimal expression of the gene of interest in the target cell can be achieved.

In addition, in order to increase efficiency of packaging, the 5'LTR from one virus (e.g., MoMLV) can be used in combination with the 3' LTR of a second (e.g., GaLV). If the constructs comprise a MoMLV 5'LTR and a GaLV 3'LTR, they are efficiently expressed in murine packaging cells (e.g., PG13) but result in proviral DNA comprising promoter sequences from GaLV which function more efficiently in human cells. These constructs are efficiently packaged in packaging cells such as PG13 because the 5' MoMLV LTR drives gene transcription in the packaging cells. However, when the packaged retroviral vector is infected into an appropriate target cell, the 3' GaLV promoter drives gene transcription (see Example 3, herein). Examples of retroviral vectors with MoMLV 5' LTR's and packaging signals and 3'GaLV LTR's include plasmids 521 and 537, described in Example 3, herein. This type of retroviral vector has the advantages of both efficient packaging in cell lines such as PG13 and higher expression in various target cells (see Example 4, herein).

The cis-acting packaging sequences used in the defective viral genomes may be derived from GaLV SEATO. The minimal sequences required for efficient packaging of a GaLV-based defective genome are described herein. In particular, as shown in detail below, the first 910 to 1290 nucleotides from the 5' end of the GaLV SEATO genome can direct packaging of a defective genome by PG13 and PA317 cells. This result also shows that the sequences required for efficient packaging from GaLV are recognized by MoMLV core proteins. Thus, hybrid retroviral vectors comprising both GaLV and MoMLV components can be conveniently constructed.

The GaLV SEATO sequences required for packaging of the defective genomes include the 5' LTR and extend to about position 1290 of the GaLV genome illustrated in FIG. 1. The sequences required for packaging also include the packaging site, ψ, which is typically defined negatively as a sequence which, when deleted from a viral genome, prevents efficient packaging of the genome. In the GaLV SEATO genome, ψ is located downstream of the 5' LTR beginning at about position 200. The site usually comprises at least about 350 bp, preferably between about 500 bp and about 1500 bp, more preferably about 700 to about 1200 bp. One of skill will recognize that minor modifications to the packaging sequence shown in FIG. 1 will not substantially affect the ability of the sequence to direct packaging. Thus, the term "GaLV packaging site" as used herein refers to GaLV DNA sequences, or RNA sequences transcribed from them which are capable of directing packaging when present in cis in a GaLV genome or defective genome. The term "GaLV SEATO packaging sites" refers to those DNA or RNA sequences substantially identical (as determined above) to the disclosed sequences and which are functional in the defective GALV genomes of the present invention.

The retroviral vectors of the invention are suitable for delivering a variety of polynucleotides to cells, including transgenes for augmenting or replacing endogenous genes in gene therapy or for the production of transgenic animals. Antisense polynucleotides can be used to control expression of target endogenous genes such as oncogenes. In addition, genes encoding toxins can be targeted for delivery to cancer cells. Other suitable sequences include those encoding growth substances to promote immune responses to cancers or infections, soluble factors to modulate receptor activity, and the like. The inserted polynucleotide of interest should be less than about 10 kb, preferably between about 7 and 8 kb.

In certain embodiments, homologous targeting constructs are used to replace an endogenous target gene. Methods and materials for preparing such constructs are known by those of skill in the art and are described in various references. See, e.g., Thomas et al., *Cell* 51:503 (1987) and Capecchi, *Science* 244:1288 (1989), which are incorporated herein by reference.

Homologous targeting constructs have at least one region having a sequence that substantially corresponds to, or is substantially complementary to, a predetermined endogenous target gene sequence (e.g., an exon sequence, an enhancer, a promoter, an intronic sequence, or a flanking sequence of the target gene). Such a homology region serves as a template for homologous pairing and recombination with substantially identical endogenous gene sequence(s). In the targeting of transgenes, such homology regions typically flank the replacement region, which is a region of the targeting transgene that is to undergo replacement with the targeted endogenous gene sequence. Thus, a segment of the targeting transgene flanked by homology regions can replace a segment of the endogenous gene sequence by double crossover homologous recombination.

In addition, the constructs for both homologous targeting and random integration will comprise a selectable marker gene to allow selection of cells. Frequently, multiple selectable marker genes are incorporated, such as in positive-negative selection constructs for homologous gene targeting.

A selectable marker gene expression cassette typically comprises a promoter which is operational in the targeted host cell linked to a structural sequence that encodes a protein that confers a selectable phenotype on the targeted host cell, and a polyadenylation signal. A promoter included in an expression cassette may be constitutive, cell type-specific, stage-specific, and/or modulatable (e.g., by hormones such as glucocorticoids; MMTV promoter), but is expressed prior to and/or during selection.

When the selectable marker is contained in a homologous targeting construct, homologous recombination at the targeted endogenous site(s) can be chosen to place the selectable marker structural sequence downstream of a functional endogenous promoter, and it may be possible for the targeting construct replacement region to comprise only a structural sequence encoding the selectable marker, and rely upon an endogenous promoter to drive transcription. Similarly, an endogenous enhancer located near a targeted endogenous site may be relied on to enhance transcription of selectable marker gene sequences in enhancerless constructs.

Suitable selectable marker genes include, for example: gpt (encoding xanthine-guanine phosphoribosyltransferase), which can be selected for with mycophenolic acid; neo (encoding neomycin phosphotransferase), which can be selected for with G418, and DFHR (encoding dihydrofolate reductase), which can be selected for with methotrexate. Other suitable selectable markers will be apparent to those in the art.

Selection for correctly targeted recombinant cells will generally employ at least positive selection, wherein a selectable marker gene expression cassette encodes and expresses a functional protein (e.g., neo or gpt) that confers a selectable phenotype to targeted cells harboring the endogenously integrated expression cassette, so that, by addition of a selection agent (e.g., G418, puromycin, or mycophenolic acid) such targeted cells have a growth or survival advantage over cells which do not have an integrated expression cassette.

Cells harboring the transgene of interest either randomly integrated or integrated by homologous recombination may be further identified using techniques well known in the art. For instance, the cells can be screened using Southern blotting or the polymerase chain reaction (PCR). If targeted integration is being screened, the oligonucleotide probes or PCR primers should bracket recombination junctions that are formed upon transgene integration at the desired homologous site.

Gene Therapy

The retroviral vectors of the invention are particularly suitable for delivering polynucleotides to cells for gene therapy of a number of diseases. Current strategies for gene therapy are reviewed in Friedmann, *Science* 244:1275 (1989), which is incorporated herein by reference.

Delivery of the polynucleotide of interest may be accomplished in vivo by administration of the vectors to an individual patient, typically by systemic administration (e.g., intravenous, intraperitoneal, intramuscular, subdermal, or intracranial infusion). Alternatively, the vectors may be used to deliver polynucleotides to cells ex vivo such as cells explanted from an individual patient (e.g., tumor-infiltrating lymphocytes, bone marrow aspirates, tissue biopsy) or universal donor hematopoietic stem cells, followed by reimplantation of the cells into a patient, usually after selection for cells which have incorporated the polynucleotide.

The vectors may be used for gene therapy to treat congenital genetic diseases, acquired genetic diseases (e.g., cancer), viral diseases (e.g., AIDS, mononucleosis, herpesvirus infection, cytomegalovirus infection, papillomavirus infection) or to modify the genome of selected types of cells of a patient for any therapeutic benefit. Treatable disorders include hemophilia, thalassemias, ADA deficiency, familial hypercholesterolemia, inherited emphysema, cystic fibrosis, Duchenne's muscular dystrophy, lysosomal storage diseases, Gaucher's disease, and chronic granulomatous disease.

The vectors of the invention can be used to introduce polynucleotides into a variety of cells and tissues including myeloid cells, bone marrow cells, lymphocytes, hepatocytes, fibroblasts, lung cells, and muscle cells. For example, polynucleotides conferring resistance to a chemotherapeutic agent may be transferred to non-neoplastic cells, especially hematopoietic cells. Alternatively, polynucleotides comprising a toxin gene (e.g., ricin or diphtheria toxin) expression cassette or a negative selectable marker gene expression cassette may be selectively inserted into neoplastic cells. Expression of the toxin gene or negative selection gene (followed by negative selection) selectively kills target cells. Polynucleotides which are not cytotoxic but which reverse or suppress the neoplastic phenotype (e.g. antisense inhibition of oncogene expression) also may be used to treat cancer, as well. Other uses include the introduction of immunomodifiers into bone marrow cells to treat cancers.

Transgenic Animals

As noted above, the vectors of the present invention are particularly useful for gene targeting mediated by homologous recombination between a targeting polynucleotide construct and a homologous chromosomal sequence. In addition to gene therapy, such strategies are also useful for the production of transgenic animals.

The ability to introduce new genes into the germ line of an animal has been extremely valuable for basic understanding of gene expression. The improvement of desired traits in agricultural or domesticated animals is also possible using these techniques. For example, potential new traits that may be introduced include sterility in meat producing strains of cattle, or fertility and milk production in dairy cows. Other commercially desirable properties include hardiness and rapid weight gain in livestock, or "show qualities" in domestic animals such as dogs and cats. For a review of the genetic engineering of livestock see, Pursel et al, *Science* 244:1281 (1989), which is incorporated herein by reference.

Typically, embryonic stem (ES) cells are used as the transgene recipients. Cells containing the newly engineered gene are injected into a host blastocyst, which is reimplanted into a recipient female. Some of these embryos develop into chimeric animals that possess germ cells partially derived from the mutant cell line. By breeding the chimeric animals it is possible to obtain a new line containing the introduced gene.

The following examples are provided by way of illustration, not limitation.

EXAMPLE 1

Construction of GaLV Infectious Clone Comprising GaLV SEATO and GaLV SF Sequences.

To prepare the GaLV infectious clone, a missing fragment of about 250 kb from the pol gene of a GaLV SEATO clone was replaced with the corresponding sequence from GaLV SF. The following steps correspond to the numbered steps illustrated in FIGS. 1A–1F.

The steps illustrated in FIG. 1A show repair of pol gene of GaLV-SEATO.

1 The approximately 8.5 kb permuted GaLV-SEATO provirus (pGAS-2 Hd1) from pGAS-2 (Gelman et al., 1982, supra) was isolated by HindIII digestion and DEAE-cellulose membrane interception in an agarose gel. An approximately 250 bp GaLV-SF pol gene fragment of pGV-3 corresponding to the missing pol fragment of PGAS-2 was isolated by HindIII digestion and DEAE-cellulose membrane interception in an agarose gel.

2 The two DNA species were ligated at low concentration to favor circularization over multimer formation.

3 After ligated material was precipitated, Sal I restriction was used to linearize the construct.

4 The construct was ligated into Sal I-restricted and phosphatased pVZ-1 vector.

5 DH5αF' cells were transformed.

6. Transformants were screened by alkaline lysis, plasmid mini-preps, and sequencing with "GVGAS 10" primer to check number and orientation of GaLV-SF pol fragment inserts within GaLV-SEATO sequence. A clone with correct construction was named intermediate Clone 66.

Figure 1B:
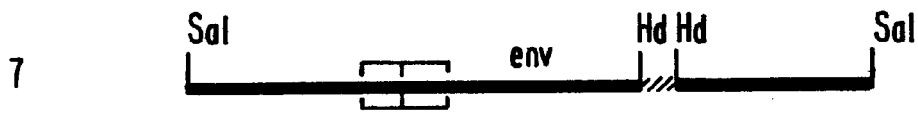
Figure 1B:
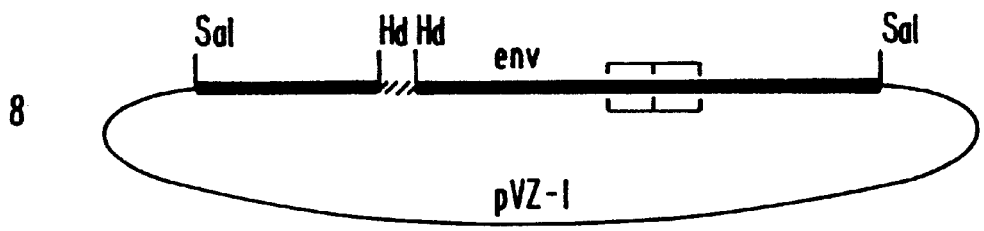
Figure 1B:
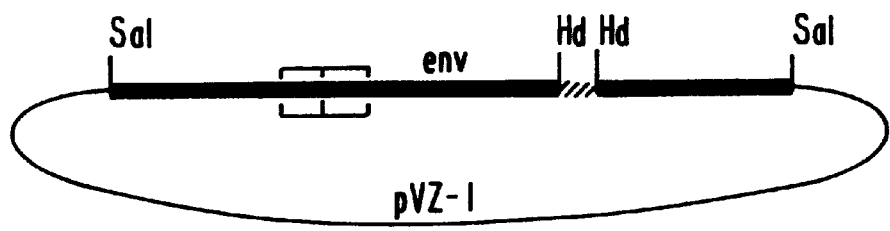

FIG. 1B shows change of GaLV-SEATO insert orientation.

7 The permuted proviral Clone 66 insert was isolated by Sal I digestion and DEAE-cellulose membrane interception on an agarose gel.

8 The insert was re-ligated back into pVZ-1 Sal I-cut and phosphatased vector to obtain opposite orientation. The opposite orientation clone was named intermediate Clone 120.

Figure 1C:
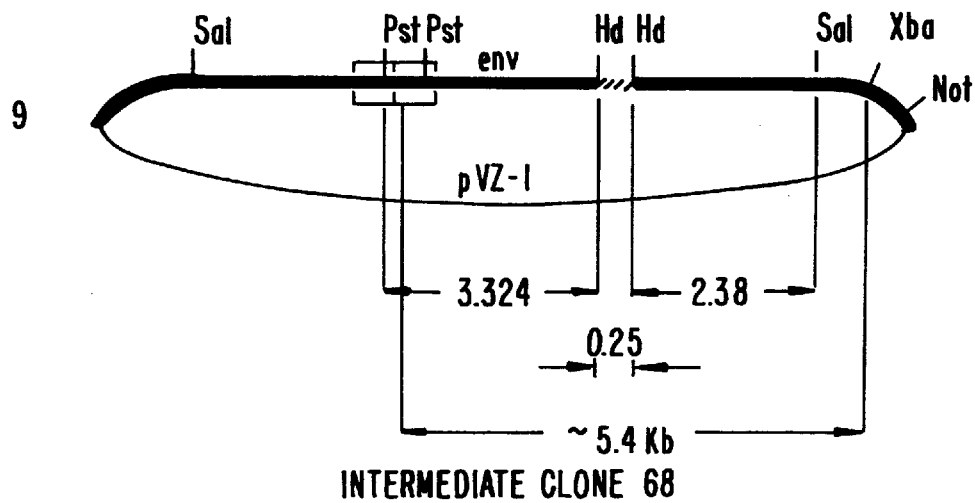
Figure 1C:
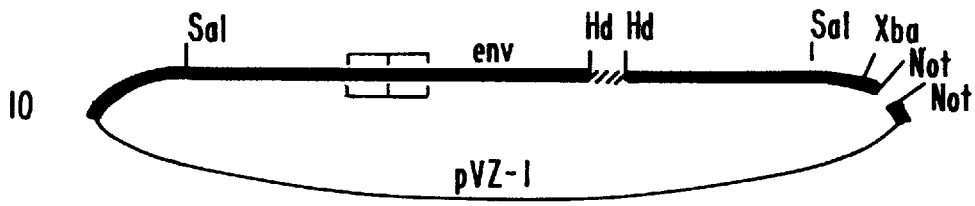
Figure 1C:
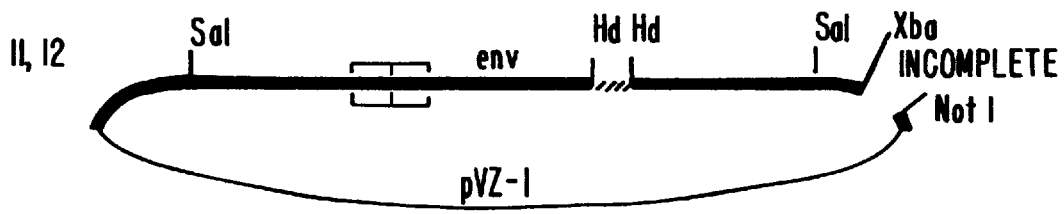
Figure 1D:
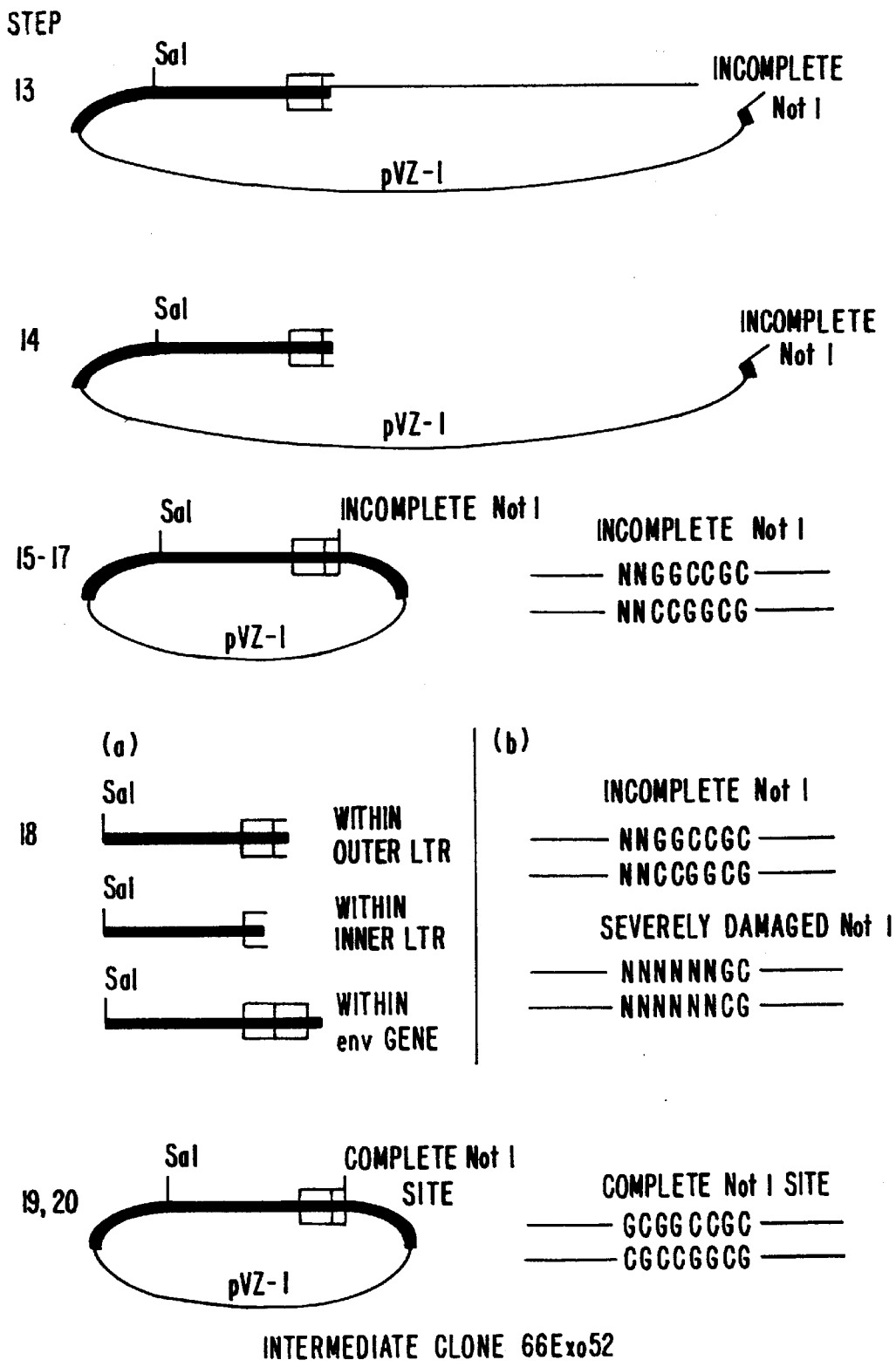

FIGS. 1C and 1D illustrate the intermediate Clone 66 and the unidirectional decrease in insert length using Exonucleases III and VII.

9 Intra-insert distances were estimated by known sequence and accurate restriction mapping. The goal was to decrease the 8.5 kb insert by 5.4 kb, stopping at a point just 3' of the LTR-LTR junction, leaving one LTR intact. The size of resulting clone (vector+insert) was ~6 kb.

10 Not I restriction of Clone 66 and Clone 120 was used to check for absence of intra-insert sites. They were found to be absent. Clone 66 was linearized with Not I in the multiple cloning site.

11 The Not I termini were filled in with cold dCTP[αS] and dGTP[αS] and DNA polymerase I (Klenow). α-thiodeoxyribonucleotides were used to block these termini from Exonuclease III digestion.

12 Clone 66 and Clone 120 were restricted with Xba I to check for absence of intra-insert sites. Clone 66 was restricted with Xba I in the multiple cloning site generating 5' overhang cohesive termini.

13 Precisely timed Exonuclease III digestion destroyed the Xba I site but the Sal I site at 5' insert end was left intact, and incomplete Not I site was resistant to attack by Exonuclease III.

14 Digestion with Exonuclease VII was used to remove remaining single strand.

15 The "ragged ends" were filled in with DNA polymerase (Klenow) and cold deoxynucleotide triphosphates.

16 The blunt ended incomplete Not I site was ligated to insert sequence.

17 DH5αF' cells were transformed.

18 Transformants were screened by alkaline lysis, plasmid mini-preps, Sal I linearization and sequencing to determine (a) extent of insert deletion and (b) quality of incomplete Not I sites and the true extent of protection given by α-thiodeoxyribonucleotides from digestion into the vector by Exonuclease III or VII.

19 Transformants were further screened by Not I digestion, searching for complete Not I site.

20 Clones that linearize with Not I were linearized to confirm presence of complete Not I site and accurately determine extent of insert deletion. One clone with desired digestion to a point just 3' of the LTR-LTR junction and with a complete Not I site, was named intermediate Clone 66Exo52.

Figure 1E:
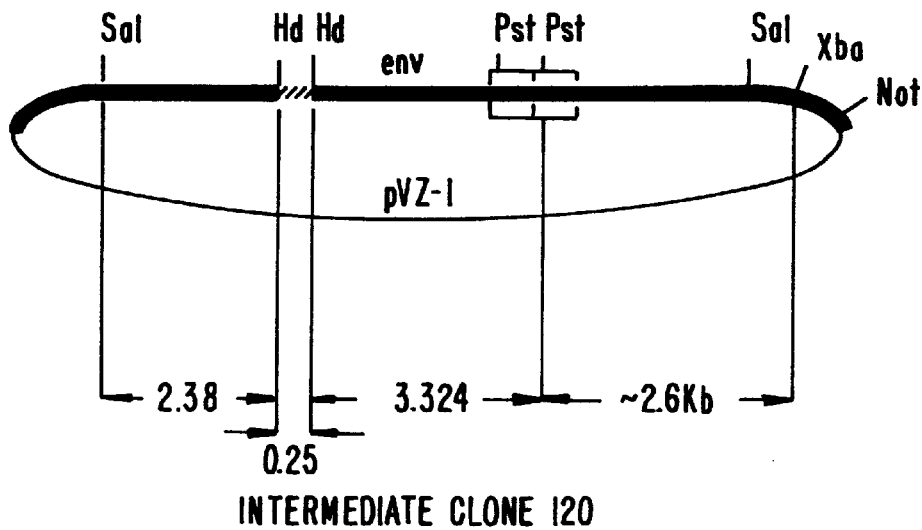
Figure 1E:
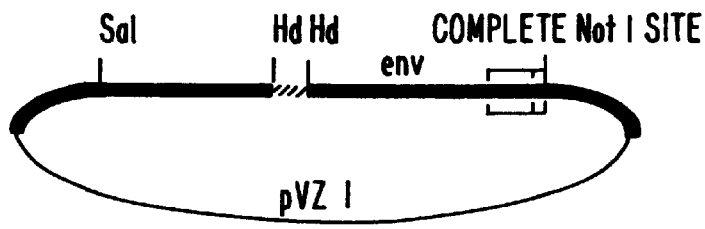

FIG. 1E shows the intermediate Clone 120: Unidirectional decrease in insert length using Exonucleases III and VII.

21 Intra-insert distance was estimated by known sequence and accurate restriction mapping. The goal was to decrease the 8.5 kb insert by 2.6 kb, stopping at a point just 3' of the LTR-LTR junction leaving one LTR intact. Size of resulting clone was ~9 kb.

22 to 32 The steps were preformed as described for steps 10–20. One clone with desired digestion to a point just 3' of the LTR-LTR junction and with a complete Not I site, was named Intermediate Clone 120Exo55.

Figure 1F:
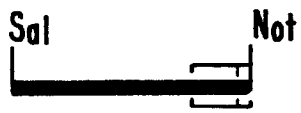
Figure 1F:
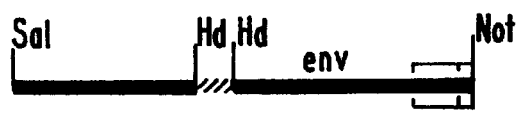
Figure 1F:
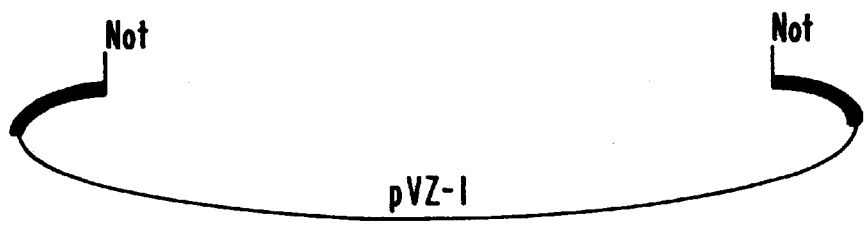
Figure 1F:
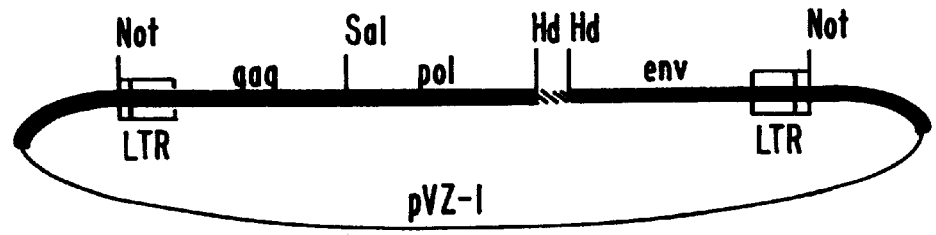

FIG. 1F shows coupling of Clone 66Exo52 insert and Clone 120Exo55 insert: separation of LTR's and generation of infectious clone.

33 Double digestion of both Clone 66Exo52 and Clone 120Exo55 with Sal I and Not I was used to release inserts.

34 Inserts were isolated by DEAE cellulose membrane interception in agarose gels.

35 Ligation of Clone 66Exo52 insert, Clone 120Exo55 insert and Not I restricted pVZ-vector.

36 DH5αF' cells were transformed.

37 Screening of transformants by $^{32}$P-labelled probing of colonies, alkaline lysis plasmid mini-preps, restriction analysis and sequencing to search for potential infectious clones with correct construction.

38 Large scale plasmid preparation and restriction mapping of GaLV-SEATO infectious clone.

The resulting cloned GaLV genome was subsequently shown to encode infectious GaLV virions.

EXAMPLE 2
Construction of Defective Genomes Comprising GaLV SF and GaLV SEATO Packaging Sites.

The steps used to prepare a defective genome comprising GaLV SEATO sequences from the infectious clone in Example 1 were as follows.

1. A 1667 bp Not I-Bgl II fragment from the 5' end of the infectious clone of GaLV SEATO was isolated.
2. A 3116 bp Bam HI-Xba I fragment corresponding to the Lac Z gene was isolated from the p1203 Lac Z plasmid (Ghattas et al., supra).
3. A 596 bp Xba I to Hind III fragment corresponding to the ECMV IRES (ECMV internal ribosome entry site) was isolated from pLZIC2 (Ghattas et al., supra).
4. A 890 bp Stu I- Sfu I fragment corresponding to the G418 resistance gene was isolated from pRcCMV plasmid (Invitrogen).
5. A 995 bp Stu I-Not I fragment corresponding to the 3' end of the GaLV SEATO infectious clone was isolated.
6. A linearized Not I pGem 13 plasmid (Promega, 318 lbp) was isolated.
7. These fragments were ligated together to assemble the pGaLV SEATO 395 plasmid.

Figure 2:
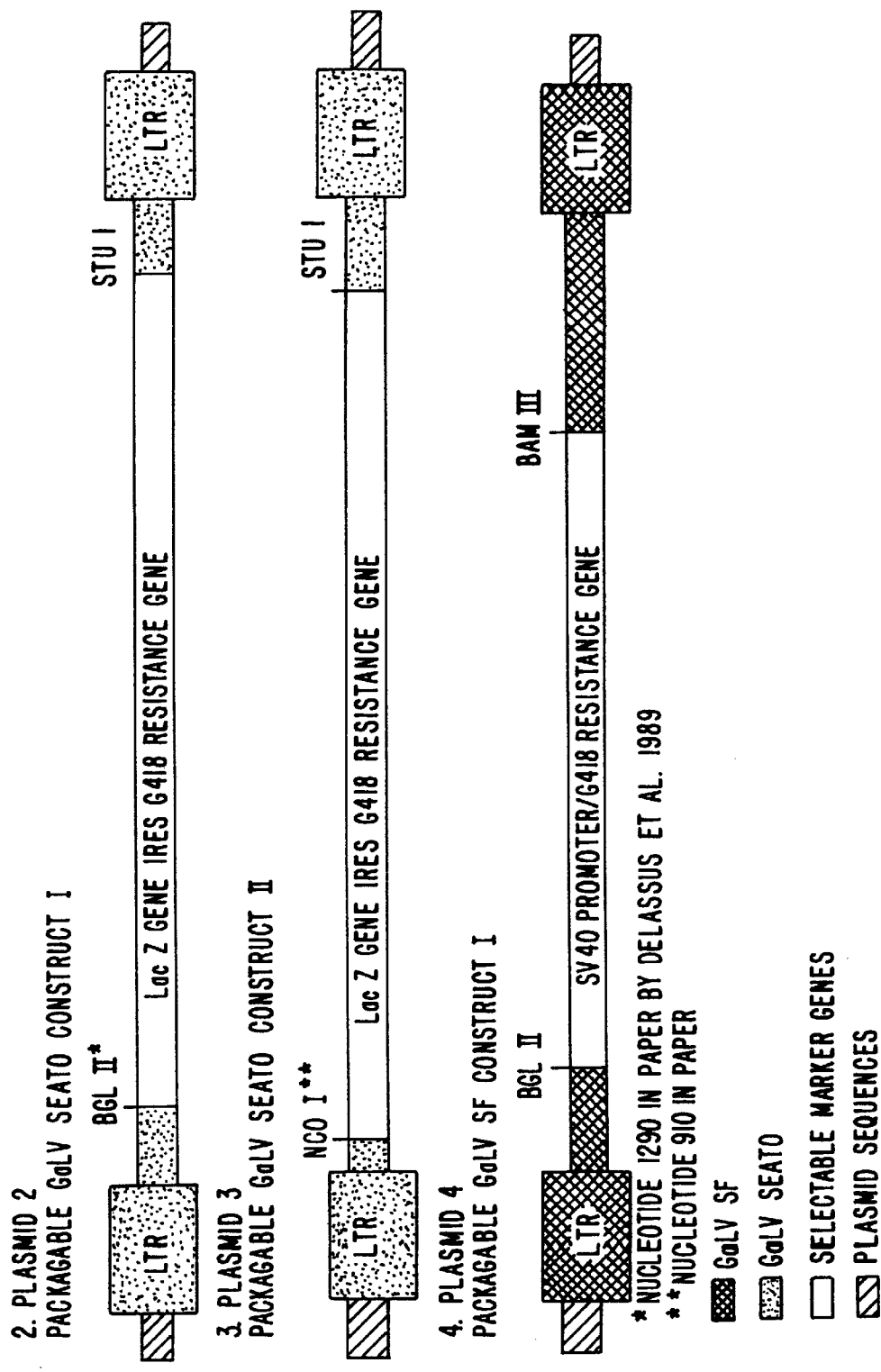
FIG. 2 shows packagable defective genomes of the present invention.
Figure 3:
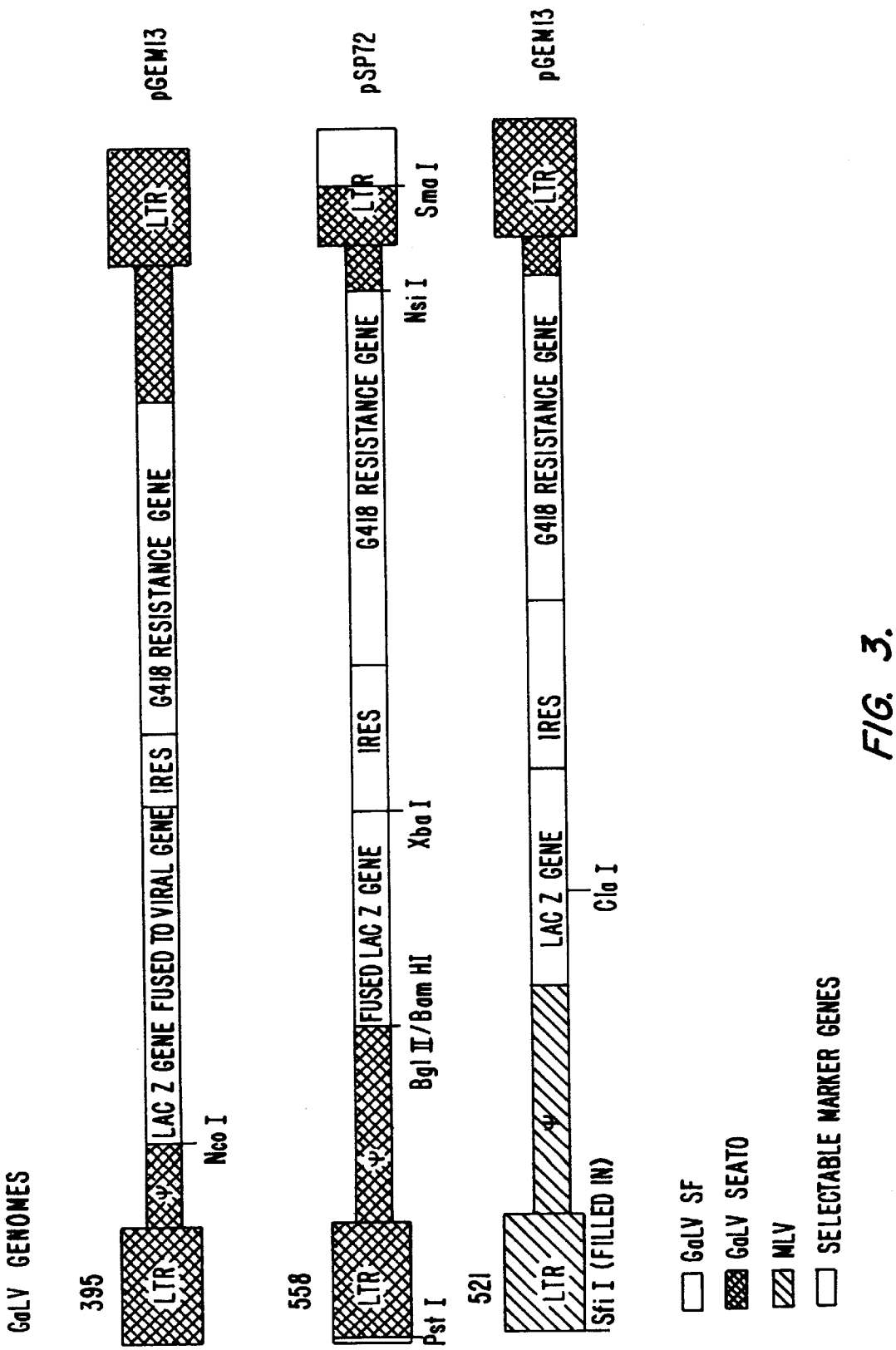
FIG. 3 shows schematic diagrams of plasmids 395, 558, and 521.

FIG. 2 (top) shows the resulting defective genome. FIG. 3 (middle) shows a defective genome constructed in the same manner but using a Not I-Nco I fragment from the 5' end of the GaLV SEATO genome. FIG. 3 (bottom) shows a construct prepared from GaLV SF sequences.

The pGaLV SEATO 395 plasmid was further modified by increasing the length of the 5' putative packaging region by 328 bp in creating the GaLV SEATO 558 construct. Plasmid 558 this represents a modified 395 plasmid which contains an additional 328 nucleotides of 5' GaLV SEATO sequences extending to the Bgl II site at position 1290 of the GaLV genome. (Plasmid 395 extends only to the Nco I site at position 910 of the GaLV genome.) The 558 plasmid construction was made using the 194 GaLV SF plasmid. The GaLV SF 194 plasmid contains a truncated GaLV SF genome cloned into the Promega pSP72 genome at the Eco RI site.

The steps in construction of the 558 plasmid are listed below.

1. A Pst I- Bgl II fragment of GaLV SEATO containing the 5' GaLV SEATO LTR and the GaLV SEATO packaging site was used to replace the corresponding region of the GaLV SF 194 plasmid partial genome.
2. A Bam HI-Xba I fragment containing the bacterial Lac Z gene but lacking an initiation codon was ligated, in reading frame, to the Bgl II site such that the Lac Z gene initiated from the GaLV SEATO gag protein translation start codon. Therefore the β-galactosidase protein is a GaLV SEATO gag-Lac Z fusion protein.
3. An Xba I to Nsi I fragment containing the EMCV IRES and a G418 gene was ligated to the Xba I site downstream of the Lac Z gene and the Nsi I in the 3' region of the GaLV SF 194 genome.
4. The Nsi I- Sma I region at the 3' end of the 194 GaLV SF genome was replaced with a corresponding region of GaLV SEATO, such that the 3' U3 of the LTR contained GaLV SEATO derived sequences in place of the GaLV SF 194 sequences.

The schematic diagrams of plasmids 395 and 558 are compared in FIG. 3 and the nucleotide sequence of plasmid 558 is shown in Seq. ID No. 3.

EXAMPLE 3
Construction of GALV Defective Genomes with Improved Packaging Efficiency in Murine Packaging Cell Lines that Express MoMLV Structural Proteins In order to improve the efficiency of packaging in murine packaging cell lines such as PG13 and PA317, which express MoMLV structural proteins, we constructed GALV defective genomes that have a MoMLV promoter at the 5' end and a GaLV promoter at the 3' end.

Two defective genomes, designated plasmid 521 and plasmid 537, having a MoMLV promoter at the 5' end and a GaLV promoter at the 3' end, were constructed. In order to construct plasmid 521, the 5' end of the 395 plasmid (Sfi I/filled in-Cla I) was replaced with the corresponding fragment of a similar MoMLV-based Lac Z genome (Sst II/filled in to Cla I). In order to construct plasmid 537, the 3' Nsi I-Not I (filled in) fragment of 521 was replaced with Nsi-Bgl II (filled in) fragment of GaLV SF 194.

Figure 4:
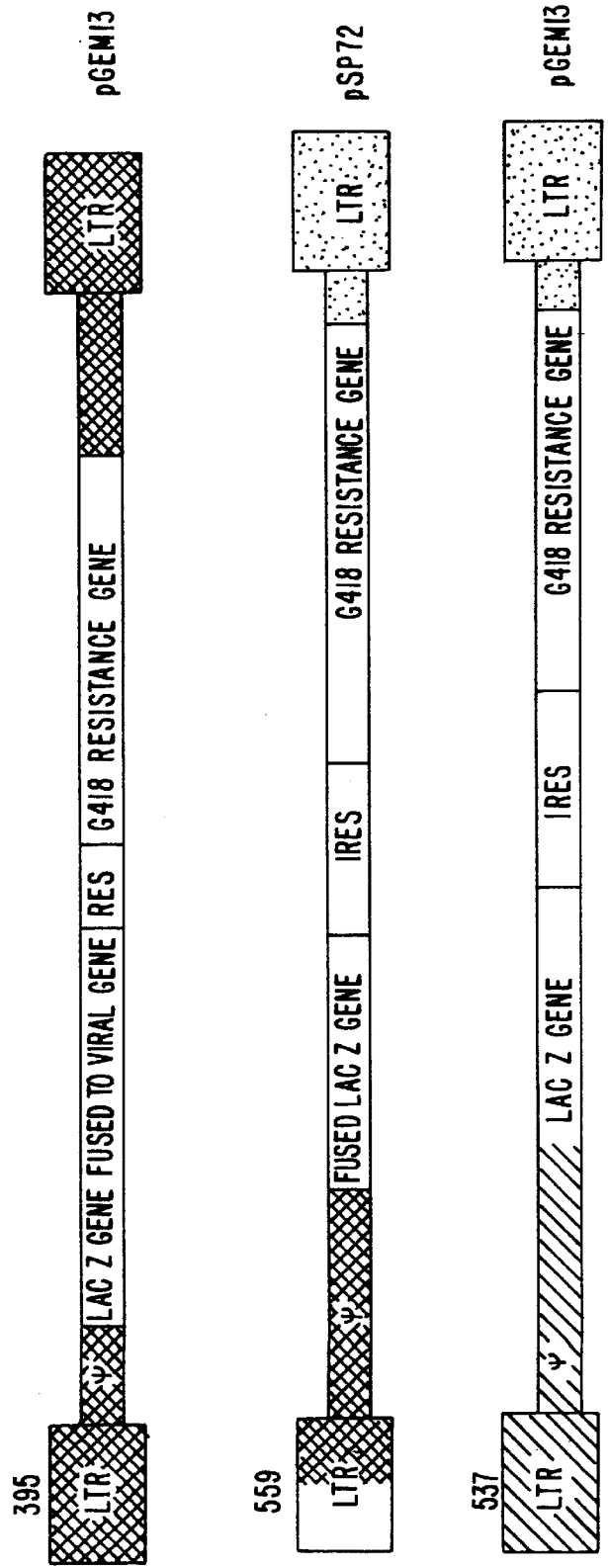
FIG. 4 shows schematic diagrams of plasmids 395, 559 and 537.

For comparative purposes, a MoMLV defective genome plasmid similar in construction to the 521 plasmid, was prepared by replacing the Spe I- Sph I fragment of pLXSN (which contains the end of the MoMLV packaging region, the SV40 promoter and the 5' part of the G418 gene with the corresponding region (also an Spe I-Sph fragment) of the 521 genome, thereby replacing the SV40 promoter with an IRES element. This defective genome is designated plasmid 560. Plasmids 521, 537, and 560 are shown schematically in FIGS. 3 and 4. The nucleotide sequence of plasmid 521 is shown in Seq. ID No. 4 and the nucleotide sequence of plasmid 537 is shown in Seq. ID No. 5.

The 521 and 537 plasmid constructs provide a means of optimizing gene expression in the packaging cells while retaining GaLV-driven gene expression in target cells where GaLV promoters function more efficiently then the MoMLV promoter. Because the 521 and 537 constructs have a MoMLV promoter at the 5' end, cells transfected with these constructs (such as packaging cells PA317 and PG 13) have a MoMLV promoter (U3) driving gene transcription. On the other hand, when the genome is reverse transcribed after infection of the target cell, the GaLV U3 promoter in the 3' LTR is duplicated and replaces the MoMLV promoter at the 5' end. This has been demonstrated by sequence analysis of unintegrated vector DNA from 521 target cells (data not shown). The DNA from these cells infected with the 521 construct after packaging in either PG13 or PA317 cells contains a 5' AND 3' GaLV SEATO U3 (data not shown). Therefore the 5' end of the 521 genome switches from a MoMLV U3 to a GaLV SEATO U3 in infected cells, which results in GaLV-driven gene expression in target cells.

EXAMPLE 4
Effect of the Number of 45 bp Enhancer Elements in the U3 Region of the GaLV LTR on Efficiency of Gene Expression in Target Cells There are a variable number of repetitive 45 bp enhancer elements in the U3 region of the GaLV LTR. The 558 plasmid and the 521 plasmid U3 regions, derived from GaLV SEATO, each contain 3 repetitive 45 bp enhancer elements, whereas GaLV SF (eg. plasmids 537 and 559) has only one of these elements. The number of repeats may play a restrictive but potentially useful role in governing expression of downstream genes in different target cells. The experimental data presented below suggests that the number of repetitive 45 bp enhancer elements in the U3 region of the LTR of GaLV can effect the efficiency of tissue/cell specific gene expression.

Following transfection of the 521, 537 or 560 plasmids into the PA317 or PGI3 cell lines, the MoMLV promoters are used to express packagable genomes. For the 521 and 537 plasmids, however, the GaLV promoter is used to express β-galactosidase and G418 resistance in the target cell after infection with the packaged defective genomes. The effect of three repeats of the 45 base pair enhancer region versus only one copy of the enhancer region in the GaLV promoter is shown in the table below. The expression of the G418 indicator gene is measured by titering G418 resistant colonies. The data in the table below demonstrates the effect of varying the number of 45 bp enhancer region repeats on the expression of genes driven by the GaLV LTRs in different cell types (see table).

TABLE

Efficiency of Gene Expression Directed by Retroviral Vectors in Various Target Cells

| genome | 537 | 558 | 560 |
|---|---|---|---|
| packaging cells: | PGI3 | PGI3 | PGI3 |
| promoter used | GaLV SF | GaLV SEATO | MoMLV |
| target cells: | | | |
| mink fibroblasts | $2 \times 10^{2\#}$ | $5 \times 10^4$ | 5.0 |
| murine NIH 3T3 cells | $5 \times 10^4$ | 5.0 | $5 \times 10^4$ |
| BHK hamster cells | — | $0.5 \times 10$ | — |
| HaK hamster cells | — | $0.5 \times 10^2$ | — |
| Bovine MDBK cells | $5 \times 10^3$ | $5 \times 10^4$ | $5 \times 10^2$ |
| | —* | —* | —* |
| Human KB cells | $5 \times 10^4$ | $5 \times 10^2$ | $5 \times 10$ |
| Human HeLA cells | $5 \times 10^4$ | $5 \times 10^2$ | $5 \times 10^2$ |
| Human 293 cells | $5 \times 10$ | $5 \times 10^2$ | $5 \times 10^4$ |
| | $5 \times 10^{3*}$ | $5 \times 10^*$ | $5 \times 10^{3*}$ | titer expressed as number of G418 resistant colonies obtained with I ml of PGI3 or PA317 supernatant containing retroviral vectors with either the 537, 558 or 560 genomes
*genomes packaged in PA317 cells Although the present invention has been described in some detail by way of illustration and example for purposes of clarity and understanding, it will be apparent that certain changes and modifications may be practiced within the scope of the appended claims.

What is claimed is:

1. A recombinant DNA construct comprising a replication-defective retroviral genome comprising a polynucleotide sequence of interest and a gibbon ape leukemia virus (GaLV) packaging site.

2. The construct of claim 1, wherein the packaging site consists of between about 150 base pairs and about 1500 base pairs.

3. The construct of claim 1, wherein the packaging site consists of a sequence extending from about position 570 to about position 1280 of SEQ ID NO:1.

4. The construct of claim 1, wherein the construct further comprises regulatory sequences which direct expression of the polynucleotide of interest.

5. The construct of claim 4, wherein the regulatory sequences are from a GaLV 3' LTR.

6. The construct of claim 5, wherein the regulatory sequences are from GaLV SF.

7. The construct of claim 1, wherein the construct comprises a sequence encoding the GaLV envelope (env) glycoprotein.

8. A cultured mammalian cell comprising the replication-defective viral genome of claim 1.

9. The cell of claim 8, further comprising retroviral gag and pol genes.

10. The cell of claim 9, wherein the gag and pol genes are from GaLV SF or GaLV SEATO.

11. The cell of claim 9, wherein the gag and pol genes are from MoMLV.

12. The cell of claim 8, further comprising a retroviral env gene.

13. The cell of claim 12, wherein the env gene is from GaLV SF or GaLV SEATO.

14. The cell of claim 8, which is PG13 or PA317.

15. An isolated hybrid retrovirus virion comprising, a GaLV envelope protein, an RNA genome comprising a polynucleotide sequence of interest operably linked to expression regulatory sequences, and, a GaLV packaging site.

16. The virion of claim 15, further comprising GaLV core proteins.

17. The virion of claim 15, further comprising MoMLV core proteins.

18. The virion of claim 15, wherein the envelope protein is a GaLV SF envelope protein.

19. The virion of claim 15, wherein the packaging site is transcribed from a sequence consisting of between about 150 base pairs and about 1500 base pairs.

20. The virion of claim 15, wherein the packaging site is transcribed from a polynucleotide sequence extending from about position 570 to about position 1280 of SEQ ID NO:1.

21. A method of introducing a polynucleotide sequence of interest into human cells having a GaLV receptor, comprising:

contacting the cells, in vitro, with hybrid retrovirus virions comprising, a GaLV envelope protein, an RNA genome comprising the polynucleotide sequence of interest operably linked to expression regulatory sequences, and a GaLV packaging site, selecting cells having the polynucleotide of interest.

22. The method of claim 21, wherein the human calls are selected from the group consisting of bone marrow cells and tumor infiltrating cells.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 8535 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (ix) FEATURE:
      (A) NAME/KEY: misc_feature (B) LOCATION: 1..8535
        (D) OTHER INFORMATION: /standard_name= "GaLV SEATO Genome"

(xi) SEQUENCE DESCRIPTION: SEQ ID NO:1:

```
AATGAAAGAA GTGTTTTTTT TTAGCCAACT GCAGTAACGC CATTTTGCTA GGCACACCTA      60

AAGGATAGGA AAAATACAGC TAAGAACAGG GCCAAACAGG ATATCTGTGG TCATGCACCT     120

GGGCCCCGGC CCAGGCCAAG GACAGAGGGT TCCCAGAAAT AGATGAGTCA ACAGCAGTTT     180

CCAGCAAGGA CAGAGGGTTC CCAGAAATAG ATGAGTCAAC AGCAGTTTCC AGGGTGCCCC     240

TCAACCGTTT CAAGGACTCC CATGACCGGG AATTCACCCC TGGCCTTATT TGAACTAACC     300

AATTACCTTG CCTCTCGCTT CTGTACCCGC GCTTTTTGCT ATAAAAATAA GCTCAGAAAC     360

TCCACCCGGA GCGCCAGTCC TTAGAGAGAC TGAGCCGCCC GGGTACCCGT GTGTCCAATA     420

AAACCTCTTG CTGATTGCAT CCGGAGCCGT GGTCTCGTTG TTCCTTGGGA GGGTTTCTCC     480

TAACTATTGA CCGCCCACTT CGGGGGTCTC ACATTTGGGG GCTCGTCCGG GATCGGAAAC     540

CCCACCCAGG GACCACCGAC CCACCAACGG GAGGTAAGCT GGCCAGCGAC CGTTGTGTGT     600

CTCGCTTCTG TGTCTAAGTC CGTAATTCTG ACTGTCCTTG TGTGTCTCGC TTCTGTGTCT     660

GAGACCGTAA CTCTGACTGC CCTTGTAAGT GCGCGCATTT TTTTGGTTTC AGTCTGTTCC     720

GGGTGAATCA CTCTGCGAGT GACGTGTGAG TAGCGAACAG ACGTGTTCGG GGCTCACCGC     780

CTGGTAATCC AGGGAGACGT CCCAGGATCA GGGGAGGACC AGGGACGCCT GGTGGACCCC     840

TCGGTAACGG GTCGTTGTGA CCCGATTTCA TCGCCCGTCT GGTAAGACGC GCTCTGAATC     900

TGATTCTCTC TCTCGGTCGC CTCGCCGCCG TCTCTGGTTT CTTTTTGTTT CGTTTCTGGA     960

AAGCCTCTGT GTCACAGTCT TTCTCTCCCA AATCATCAAT ATGGGACAAG ATAATTCTAC    1020

CCCTATCTCC CTCACTCTAA ATCACTGGAG AGATGTGAGA ACAAGGGCTC ACAATCTATC    1080

CGTGGAAATC AAAAAGGGAA AATGGCAGAC TTTCTGTTCC TCCGAGTGGC CACACATTCGG   1140

CGTGGGGTGG CCACCGGAGG GAACTTTTAA TCTCTCTGTC ATTTTTGCAG TTAAAAAGAT    1200

TGTCTTTCAG GAGAACGGGG GACATCCGGA CCAAGTTCCA TATATCGTGG TATGGCAGGA    1260

CCTCGCCCAG AATCCCCCAC CATGGGTGCC AGCCTCCGCC AAGGTCGCTG TTGTCTCTGA    1320

TACCCGAAGA CCAGTTGCGG GGAGGCCATC AGCTCCTCCC CGACCCCCCA TCTACCCGGC    1380

AACAGACGAC TTACTCCTCC TCTCTGAACC CACGCCCCCG CCCTATCCGG CGGCACTGCC    1440

ACCCCCTCTG GCCCCTCAGG CGATCGGACC GCCGTCAGGC CAGATGCCCG ATAGTAGCGA    1500

TCCTGAGGGG CCAGCCGCTG GGACCAGGAG TCGCCGTGCC CGCAGTCCAG CAGACAACTC    1560

GGGTCCTGAC TCCACTGTGA TTTTGCCCCT CCGAGCCATA GGACCCCGG CCGAGCCCAA     1620

TGGCCTGGTC CCTCTACAAT ATTGGCCTTT TTCCTCAGCA GATCTTTATA ATTGGAAATC    1680

TAATCATCCC TCTTTTTCTG AAAACCCAGC AGGTCTCACG GGGCTCCTTG AGTCTCTTAT    1740

GTTCTCCCAT CAGCCCACTT GGGACGATTG CCAACAGCTC CTACAGATTC TTTTCACCAC    1800

TGAGGAACGG GAAAGAATTC TCCTGGAGGC CCGCAAAAAT GTCCTTGGGG ACAATGGGGC    1860

CCCTACACAG CTCGAGAACC TCATTAATGA GGCCTTCCCC CTCAATCGAC CTCACTGGGA    1920

TTACAACACA GCCGCAGGTA GGGAGCGTCT TCTGGTCTAC CGCCGGACTC TAGTGGCAGG    1980

TCTCAAAGGG GCAGCTCGGC GTCCTACCAA TTTGGCTAAG GTAAGAGAGG TCTTGCAGGG    2040

ACCGGCAGAA CCCCCTTCGG TTTTCTTAGA ACGCCTGATG GAGGCCTATA GGAGATACAC    2100

TCCGTTTGAT CCCTCTTCTG AGGGACAACA GGCTGCGGTC GCCATGGCCT TTATCGGACA    2160

GTCAGCCCCA GATATCAAGA AAAAGTTACA GAGGCTAGAG GGGCTCCAGG ACTATTCCTT    2220
```

-continued

```
ACAAGATTTA GTAAAAGAGG CAGAAAAGGT GTACCATAAG AGAGAGACAG AAGAAGAAAG    2280

ACAAGAAAGA GAAAAAAAGG AGGCAGAAGA AAAGGAGAGG CGGCGCGATA GGCCGAAGAA    2340

AAAAAACTTG ACTAAAATTC TGGCCGCAGT AGTAAGTAGA GAAGGGTCCA CAGGTAGGCA    2400

GACAGGGAAC CTGAGCAACC AGGCAAAGAA GACACCTAGG GATGGAAGAC CTCCACTAGA    2460

CAAAGACCAG TGCGCATACT GTAAAGAGAA GGGCCATTGG GCAAGAGAAT GTCCCCGAAA    2520

AAAACACGTC AGAGAAGCCA AGGTTCTAGC CCTAGATAAC TAGGGGAGTC AGGGTTCGGA    2580

CCCCCTCCCC GAACCTAGGG TAACACTGAC TGTGGAGGGG ACCCCCATTG AGTTCCTGGT    2640

CGACACCGGA GCTGAACATT CAGTATTGAC CCAACCCATG GGAAAAGTAG GGTCCAGACG    2700

GACGGTCGTG GAAGGAGCGA CAGGCAGCAA GGTCTACCCC TGGACCACAA AAAGACTTTT    2760

AAAAATTGGA CATAAACAAG TGACCCACTC CTTCCTGGTC ATACCCGAGT GCCCTGCTCC    2820

TCTGTTGGGC AGGGACCTCC TAACCAAACT AAAGGCCCAG ATCCAGTTTT CCGCTGAGGG    2880

CCCACAGGTA ACATGGGGAG AACGCCCTAC TATGTGCCTG GTCCTAAACC TGGAAGAAGA    2940

ATACCGACTA CATGAAAAGC CAGTACCCTC CTCTATCGAC CCATCCTGGC TCCAGCTTTT    3000

CCCCACTGTA TGGGCAGAAA GAGCCGGCAT GGGACTAGCC AATCAAGTCC CACCAGTGGT    3060

AGTAGAGCTA AGATCAGGTG CCTCACCAGT GGCTGTTCGA CAATATCCAA TGAGCAAAGA    3120

AGCTCGGGAA GGTATCAGAC CCCACATCCA GAAGTTCCTA GACCTAGGGG TCTTGGTGCC    3180

CTGTCGGTCG CCCTGGAATA CCCCTCTGCT ACCTGTAAAA AAGCCAGGGA CCAATGACTA    3240

TCGGCCAGTT CAAGACCTGA GAGAAATTAA TAAAAGGGTA CAGGATATTC ATCCCACAGT    3300

CCCAAACCCT TACAATCTTC TGAGTTCCCT TCCGCCTAGC TATACTTGGT ACTCAGTCTT    3360

AGATCTCAAG GATGCCTTTT TCTGCCTCAG GCTACATCCC AACAGCCAGC CGCTGTTCGC    3420

GTTCGAGTGG AAAGACCCAG AAAAAGGTAA CACAGGTCAG CTGACCTGGA CGCGGCTACC    3480

ACAAGGGTTC AAGAACTCTC CCACTCTCTT CGACGAGGCC CTCCACCGAG ATTTGGCTCC    3540

CTTTAGGGCC CTCAACCCCC AGGTGGTGTT ACTCCAATAT GTGGACGACC TCTTGGTGGC    3600

CGCCCCCACA TATGAAGACT GCAAAAAAGG AACACAGAAG CTCTTACAGG AGTTAAGTAA    3660

GTTGGGGTAC CGGGTATCGG CTAAGAAGGC CCAGCTCTGC CAGAGAGAAG TCACCTATCT    3720

GGGGTACCTA CTCAAGGAAG GAAAAAGATG GCTAACCCCA GCCCGAAAGG CTACTGTTAT    3780

GAAAATCCCT GTTCCTACGA CCCCCAGACA GGTCCGTGAA TTTCTAGGCA CTGCCGGATT    3840

CTGCAGGCTC TGGATCCCTG GGTTTGCTTC CCTGGCTGCA CCCTTGTACC CCTAACAAA    3900

AGAGAGCATC CCTTTTATTT GGACTGAGGA ACATCAGCAG GCTTTTGACC ACATAAAAAA    3960

AGCCTTGCTG TCAGCCCCTG CATTGGCCCT CCCAGACCTC ACCAAGCCAT TCACTCTATA    4020

TATAGATGAG AGAGCCGGCG TGGCCCGGGG AGTGCTCACT CAGACTTTAG GACCCTGGCG    4080

GCGGCCAGTA GCATATCTAT CAAAAAAACT GGATCCGGTG GCCAGCGGGT GGCCAACCTG    4140

CCTGAAAGCG GTTGCAGCAG TAGCACTCCT TCTCAAAGAC GCTGATAAGT TAACCTTGGG    4200

ACAAAATGTG ACTGTGATTG CTTCCCATAG CCTCGAAAGC ATCGTGCGGC AACCCCCGA    4260

CCGGTGGATG ACCAATGCCA GAATGACTCA TTACCAGAGC CTGCTGTTAA ATGAAAGGGT    4320

ATCGTTTGCG CCCCCTGCTG TCCTAAACCC AGCTACCCTA CTTCCAGTCG AGTCGGAAGC    4380

CACCCCAGTG CACAGGTGCT CAGAAATCCT CGCCGAAGAA ACTGGAACTC GACGAGACCT    4440

AGAAGACCAA CCATTGCCCG GGGTGCCAAC CTGGTATACA GACGGTAGCA GTTTCATCAC    4500

GGAAGGTAAA CGGAGAGCAG GGGCCCCGAT CGTAGATGGC AAGCGGACGG TATGGGCTAG    4560

CAGCCTGCCA GAAGGTACGT CAGCCCAGAA GGCTGAACTA GTAGCCTTGA CGCAGGCATT    4620
```

-continued

```
ACGCCTGGCC GAAGGAAAAA ACATCAACAT CTACACGGAC AGCAGGTATG CTTTTGCCAC    4680
TGCTCATATT CATGGGGCAA TATATAAGCA GAGGGGGCTG CTCACTTCTG CTGGAAAAGA    4740
TATCAAAAAC AAAGAGGAAA TTTTGGCCCT GCTAGAGGCC ATCCATCTCC CTAGGCGGGT    4800
CGCCATTATC CACTGTCCTG GCCACCAGAG GGGAAGTAAC CCTGTGGCCA CTGGGAACCG    4860
GAGGGCCGAC GAGGCTGCAA AGCAAGCCGC CCTGTCGACC AGAGTGCTGG CAGGAACTAC    4920
AAAACCTCAA GAGCCAATCG AGCCCGCTCA AGAAAAGACC AGGCCGAGGG AGCTCACCCC    4980
TGACCGGGGA AAAGAATTCA TTAAGCGGTT ACATCAGTTA ACTCACTTAG GACCAGAAAA    5040
GCTTCTCCAA CTAGTGAACC GTACCAGCCT CCTCATCCCG AACCTCCAAT CTGCAGTTCG    5100
CGAAGTCACC AGTCAGTGTC AGGCTTGTGC CATGACTAAT GCGGTCACCA CCTACAGAGA    5160
GACCGGAAAA AGGCAACGAG GAGATCGACC CGGCGTGTAC TGGGAGGTAG ACTTCACAGA    5220
AATAAAGCCT GGTCGGTATG GAAACAAGTA TCTGTTAGTA TTCATAGATA CTTTCTCCGG    5280
ATGGGTAGAA GCTTTTCCTA CCAAAACTGA AACGGCCCTA ATCGTCTGTA AAAAAATATT    5340
AGAAGAAATT CTACCCCGCT TCGGGATCCC TAAGGTACTC GGGTCAGACA ATGGCCCGGC    5400
CTTTGTTGCT CAGGTAAGTC AGGGACTGGC CACTCAACTG GGGATAAATT GGAAGTTACA    5460
TTGTGCGTAT AGACCCCAGA GCTCAGGTCA GGTAGAAAGA ATGAACAGAA CAATTAAAGA    5520
GACCTTGACC AAATTAGCCT TAGAGACCGG TGGAAAAGAC TGGGTGACCC TCCTTCCCTT    5580
AGCGCTGCTT AGGGCCAGGA ATACCCCTGG CCGGTTTGGT TTAACTCCTT ATGAAATTCT    5640
CTATGGAGGA CCACCCCCCA TACTTGAGTC TGGAGAAACT TTGGGTCCCG ATGATAGATT    5700
TCTCCCTGTC TTATTTACTC ACTTAAAGGC TTTAGAAATT GTAAGGACCC AAATCTGGGA    5760
CCAGATCAAA GAGGTGTATA AGCCTGGTAC CGTAACAATC CCTCACCCGT TCCAGGTCGG    5820
GGATCAAGTG CTTGTCAGAC GCCATCGACC CAGCAGCCTT GAGCCTCGGT GGAAAGGCCC    5880
ATACCTGGTG TTGCTGACTA CCCCGACCGC GGTAAAAGTC GATGGTATTG CTGCCTGGGT    5940
CCATGCTTCT CACCTCAAAC CTGCACCACC TTCGGCACCA GATGAGTCCT GGGAGCTGGA    6000
AAAGACTGAT CATCCTCTTA AGCTGCGTAT TCGGCGGCGG CGGGACGAGT CTGCAAAATA    6060
AGAACCCCCA CCAGCCCATG ACCCTCACTT GGCAGGTACT GTCCCAAACT GGAGACGTTG    6120
TCTGGGATAC AAAGGCAGTC CAGCCCCCTT GGACTTGGTG GCCCACACTT AAACCTGATG    6180
TATGTGCCTT GGCGGCTAGT CTTGAGTCCT GGGATATCCC GGGAACCGAT GTCTCGTCCT    6240
CTAAACGAGT CAGACCTCCG GACTCAGACT ATACTGCCGC TTATAAGCAA ATCACCTGGG    6300
GAGCCATAGG GTGCAGCTAC CCTCGGGCTA GGACTAGAAT GGCAAGCTCT ACCTTCTACG    6360
TATGTCCCCG GGATGGCCGG ACCCTTTCAG AAGCTAGAAG GTGCGGGGGG CTAGAATCCC    6420
TATACTGTAA AGAATGGGAT TGTGAGACCA CGGGGACCGG TTATTGGCTA TCTAAATCCT    6480
CAAAAGACCT CATAACTGTA AAATGGGACC AAAATAGCGA ATGGACTCAA AAATTTCAAC    6540
AGTGTCACCA GACCGGCTGG TGTAACCCCC TTAAAATAGA TTTCACAGAC AAAGGAAAAT    6600
TATCCAAGGA CTGGATAACG GGAAAAACCT GGGGATTAAG ATTCTATGTG TCTGGACATC    6660
CAGGCGTACA GTTCACCATT CGCTTAAAAA TCACCAACAT GCCAGCTGTG GCAGTAGGTC    6720
CTGACCTCGT CCTTGTGGAA CAAGGACCTC CTAGAACGTC CCTCGCTCTC CCACCTCCTC    6780
TTCCCCCAAG GGAAGCGCCA CCGCCATCTC TCCCCGACTC TAACTCCACA GCCCTGGCGA    6840
CTAGTGCACA AACTCCCACG GTGAGAAAAA CAATTGTTAC CCTAAACACT CCGCCTCCCA    6900
CCACAGGCGA CAGACTTTTT GATCTTGTGC AGGGGGCCTT CCTAACCTTA AATGCTACCA    6960
```

```
ACCCAGGGGC CACTGAGTCT TGCTGGCTTT GTTTGGCCAT GGGCCCCCCT TATTATGAAG    7020

CAATAGCCTC ATCAGGAGAG GTCGCCTACT CCACCGACCT TGACCGGTGC CGCTGGGGGA    7080

CCCAAGGAAA GCTCACCCTC ACTGAGGTCT CAGGACACGG GTTGTGCATA GGAAAGGTGC    7140

CCTTTACCCA TCAGCATCTC TGCAATCAGA CCCTATCCAT CAATTCCTCC GGAGACCATC    7200

AGTATCTGCT CCCCTCCAAC CATAGCTGGT GGGCTTGCAG CACTGGCCTC ACCCCTTGCC    7260

TCTCCACCTC AGTTTTTAAT CAGACTAGAG ATTTCTGTAT CCAGGTCCAG CTGATTCCTC    7320

GCATCTATTA CTATCCTGAA GAAGTTTTGT TACAGGCCTA TGACAATTCT CACCCCAGGA    7380

CTAAAAGAGA GGCTGTCTCA CTTACCCTAG CTGTTTTACT GGGGTTGGGA ATCACGGCGG    7440

GAATAGGTAC TGGTTCAACT GCCTTAATTA AAGGACCTAT AGACCTCCAG CAAGGCCTGA    7500

CAAGCCTCCA GATCGCCATA GATGCTGACC TCCGGGCCCT CCAAGACTCA GTCAGCAAGT    7560

TAGAGGACTC ACTGACTTCC CTGTCCGAGG TAGTGCTCCA AAATAGGAGA GGCCTTGACT    7620

TGCTGTTTCT AAAAGAAGGT GGCCTCTGTG CGGCCCTAAA GGAAGAGTGC TGTTTTTACA    7680

TAGACCACTC AGGTGCAGTA CGGGACTCCA TGAAAAAACT CAAAGAAAAA CTGGATAAAA    7740

GACAGTTAGA GCGCCAGAAA AGCCAAAACT GGTATGAAGG ATGGTTCAAT AACTCCCCTT    7800

GGTTCACTAC CCTGCTATCA ACCATCGCTG GGCCCCTATT ACTCCTCCTT CTGTTGCTCA    7860

TCCTCGGGCC ATGCATCATC AATAAGTTAG TTCAATTCAT CAATGATAGG ATAAGTGCAT    7920

GTTAAAATTC TGGTCCTTAG ACAAAATATC AGGCCCTAGA GAACGAAGGT AACCTTTAAT    7980

TTTGCTCTAA GATTAGAGCT ATTCACAAGA GAAATGGGGG AATGAAAGAA GTGTTTTTTT    8040

TTAGCCAACT GCAGTAACGC CATTTTGCTA GGCACACCTA AAGGATAGGA AAAATACAGC    8100

TAAGAACAGG GCCAAACAGG ATATCTGTGG TCATGCACCT GGGCCCCGGC CCAGGCCAAG    8160

GACAGAGGGT TCCCAGAAAT AGATGAGTCA ACAGCAGTTT CCAGCAAGGA CAGAGGGTTC    8220

CCAGAAATAG ATGAGTCAAC AGCAGTTTCC AGGGTGCCCC TCAACCGTTT CAAGGACTCC    8280

CATGACCGGG AATTCACCCC TGGCCTTATT TGAACTAACC AATTACCTTG CCTCTCGCTT    8340

CTGTACCCGC GCTTTTTGCT ATAAAATAAG CTCAGAAACT CCACCCGGAG CGCCAGTCCT    8400

TAGAGAGACT GAGCCGCCCG GGTACCCGTG TGTCCAATAA AACCTCTTGC TGATTGCATC    8460

CGGAGCCGTG GTCTCGTTGT TCCTTGGGAG GGTTTCTCCT AACTATTGAC CGCCCACTTC    8520

GGGGGTCTCA CATTT                                                   8535

(2) INFORMATION FOR SEQ ID NO:2:

(i) SEQUENCE CHARACTERISTICS:
        (A) LENGTH: 564 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: LTR
        (B) LOCATION: 1..564
        (D) OTHER INFORMATION: /standard_name= "3' LTR of GaLV
             SEATO"

(xi) SEQUENCE DESCRIPTION: SEQ ID NO:2:

AATGAAAGAA GTGTTTTTTT TTAGCCAACT GCAGTAACGC CATTTTGCTA GGCACACCTA     60

AAGGATAGGA AAAATACAGC TAAGAACAGG GCCAAACAGG ATATCTGTGG TCATGCACCT    120

GGGCCCCGGC CCAGGCCAAG GACAGAGGGT TCCCAGAAAT AGATGAGTCA ACAGCAGTTT    180
```

```
CCAGCAAGGA CAGAGGGTTC CCAGAAATAG ATGAGTCAAC AGCAGTTTCC AGCAAGGACA      240

GAGGGTTCCC AGAAATAGAT GAGTCAACAG CAGTTTCCAG AGGGTGCCCC TCAACCGTTT      300

CAAGGACTCC CATGACCGGG AATTCACCCC TGGCCTTATT TGAACTAACC AATTACCTTG      360

CCTCTCGCTT CTGTACCCGC GCTTTTTGCT ATAAAAATAA GCTCAGAAAC TCCACCCGGG      420

CGCCAGTCCT TAGAGAGACT GAGCCGCCCG GGTACCCGTG TGTCCAATAA AACCTCTTGC      480

TGATTGCATC CGGAGCCGTG GTCTCGTTGT TCCTTGGGAG GGTTTCTCCT AACTATTGAC      540

CGCCCACTTC GGGGGTCTCA CATT                                            564

(2) INFORMATION FOR SEQ ID NO:3:

(i) SEQUENCE CHARACTERISTICS:
        (A) LENGTH: 9661 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..9613
        (D) OTHER INFORMATION: /standard_name= "p558 retoviral
            vector"

(xi) SEQUENCE DESCRIPTION: SEQ ID NO:3:

ATTTAGGTGA CACTATAGAA CTCGAGGAAT TCTGAAAGAA GTGTTTTTCA AGTTAGCTGC       60

AGTAACGCCA TTTTGCTAGG CACACCTAAA GGATAGGAAA AATACAGCTA AGAACAGGGC      120

CAAACAGGAT ATCTGTGGTC ATGCACCTGG GCCCCGGCCC AGGCCAAGGA CAGAGGGTTC      180

CCAGAAATAG ATGAGTCAAC AGCAGTTTCC AGCAAGGACA GAGGGTTCCC AGAAATAGAT      240

GAGTCAACAG CAGTTTCCAG GGTGCCCCTC AACCGTTTCA AGGACTCCCA TGACCGGGAA      300

TTCACCCCTG GCCTTATTTG AACTAACCAA TTACCTTGCC TCTCGCTTCT GTACCCGCGC      360

TTTTTGCTAT AAAAATAAGC TCAGAAACTC CACCCGGAGC GCCAGTCCTT AGAGAGACTG      420

AGCCGCCCGG GTACCCGTGT GTCCAATAAA ACCTCTTGCT GATTGCATCC GGAGCCGTGG      480

TCTCGTTGTT CCTTGGGAGG GTTTCTCCTA ACTATTGACC GCCCACTTCG GGGGTCTCAC      540

ATTTGGGGGC TCGTCCGGGA TCGGAAACCC CACCCAGGGA CCACCGACCC ACCAACGGGA      600

GGTAAGCTGG CCAGCGACCG TTGTGTGTCT CGCTTCTGTG TCTAAGTCCG TAATTCTGAC      660

TGTCCTTGTG TGTCTCGCTT CTGTGTCTGA GACCGTAACT CTGACTGCCC TTGTAAGTGC      720

GCGCATTTTT TTGGTTTCAG TCTGTTCCGG GTGAATCACT CTGCGAGTGA CGTGTGAGTA      780

GCGAACAGAC GTGTTCGGGG CTCACCGCCT GGTAATCCAG GGAGACGTCC CAGGATCAGG      840

GGAGGACCAG GGACGCCTGG TGGACCCCTC GGTAACGGGT CGTTGTGACC CGATTTCATC      900

GCCCGTCTGG TAAGACGCGC TCTGAATCTG ATTCTCTCTC TCGGTCGCCT CGCCGCCGTC      960

TCTGGTTTCT TTTTGTTTCG TTTCTGGAAA GCCTCTGTGT CACAGTCTTT CTCTCCCAAA     1020

TCATCAATAT GGGACAAGAT AATTCTACCC CTATCTCCCT CACTCTAAAT CACTGGAGAG     1080

ATGTGAGAAC AAGGGCTCAC AATCTATCCG TGGAAATCAA AAAGGGAAAA TGGCAGACTT     1140

TCTGTTCCTC CGAGTGGCCC ACATTCGGCG TGGGGTGGCC ACCGGAGGGA ACTTTTAATC     1200

TCTCTGTCAT TTTTGCAGTT AAAAAGATTG TCTTTCAGGA GAACGGGGGA CATCCGGACC     1260

AAGTTCCATA TATCGTGGTA TGGCAGGACC TCGCCCAGAA TCCCCCACCA TGGGTGCCAG     1320

CCTCCGCCAA GGTCGCTGTT GTCTCTGATA CCCGAAGACC AGTTGCGGGG AGGCCATCAG     1380
```

-continued

```
CTCCTCCCCG ACCCCCCATC TACCCGGCAA CAGACGACTT ACTCCTCCTC TCTGAACCCA    1440

CGCCCCCGCC CTATCCGGCG GCACTGCCAC CCCCTCTGGC CCCTCAGGCG ATCGGACCGC    1500

CGTCAGGCCA GATGCCCGAT AGTAGCGATC CTGAGGGGCC AGCCGCTGGG ACCAGGAGTC    1560

GCCGTGCCCG CAGTCCAGCA GACAACTCGG GTCCTGACTC CACTGTGATT TTGCCCCTCC    1620

GAGCCATAGG ACCCCCGGCC GAGCCCAATG GCCTGGTCCC TCTACAATAT TGGCCTTTTT    1680

CCTCAGCAGA TCCCGTCGTT TTACAACGTC GTGACTGGGA AAACCCTGGC GTTACCCAAC    1740

TTAATCGCCT TGCAGCACAT CCCCCTTTCG CCAGCTGGCG TAATAGCGAA GAGGCCCGCA    1800

CCGATCGCCC TTCCCAACAG TTGCGCAGCC TGAATGGCGA ATGGCGCTTT GCCTGGTTTC    1860

CGGCACCAGA AGCGGTGCCG GAAAGCTGGC TGGAGTGCGA TCTTCCTGAG GCCGATACTG    1920

TCGTCGTCCC CTCAAACTGG CAGATGCACG GTTACGATGC GCCCATCTAC ACCAACGTAA    1980

CCTATCCCAT TACGGTCAAT CCGCCGTTTG TTCCCACGGA GAATCCGACG GGTTGTTACT    2040

CGCTCACATT TAATGTTGAT GAAAGCTGGC TACAGGAAGG CCAGACGCGA ATTATTTTTG    2100

ATGGCGTTAA CTCGGCGTTT CATCTGTGGT GCAACGGGCG CTGGGTCGGT TACGGCCAGG    2160

ACAGTCGTTT GCCGTCTGAA TTTGACCTGA GCGCATTTTT ACGCGCCGGA GAAAACCGCC    2220

TCGCGGTGAT GGTGCTGCGT TGGAGTGACG GCAGTTATCT GGAAGATCAG GATATGTGGC    2280

GGATGAGCGG CATTTTCCGT GACGTCTCGT TGCTGCATAA ACCGACTACA CAAATCAGCG    2340

ATTTCCATGT TGCCACTCGC TTTAATGATG ATTTCAGCCG CGCTGTACTG GAGGCTGAAG    2400

TTCAGATGTG CGGCGAGTTG CGTGACTACC TACGGGTAAC AGTTTCTTTA TGGCAGGGTG    2460

AAACGCAGGT CGCCAGCGGC ACCGCGCCTT TCGGCGGTGA AATTATCGAT GAGCGTGGTG    2520

GTTATGCCGA TCGCGTCACA CTACGTCTGA ACGTCGAAAA CCCGAAACTG TGGAGCGCCG    2580

AAATCCCGAA TCTCTATCGT GCGGTGGTTG AACTGCACAC CGCCGACGGC ACGCTGATTG    2640

AAGCAGAAGC CTGCGATGTC GGTTTCCGCG AGGTGCGGAT TGAAAATGGT CTGCTGCTGC    2700

TGAACGGCAA GCCGTTGCTG ATTCGAGGCG TTAACCGTCA CGAGCATCAT CCTCTGCATG    2760

GTCAGGTCAT GGATGAGCAG ACGATGGTGC AGGATATCCT GCTGATGAAG CAGAACAACT    2820

TTAACGCCGT GCGCTGTTCG CATTATCCGA ACCATCCGCT GTGGTACACG CTGTGCGACC    2880

GCTACGGCCT GTATGTGGTG GATGAAGCCA ATATTGAAAC CCACGGCATG GTGCCAATGA    2940

ATCGTCTGAC CGATGATCCG CGCTGGCTAC CGGCGATGAG CGAACGCGTA ACGCGAATGG    3000

TGCAGCGCGA TCGTAATCAC CCGAGTGTGA TCATCTGGTC GCTGGGGAAT GAATCAGGCC    3060

ACGGCGCTAA TCACGACGCG CTGTATCGCT GGATCAAATC TGTCGATCCT TCCCGCCCGG    3120

TGCAGTATGA AGGCGGCGGA GCCGACACCA CGGCCACCGA TATTATTTGC CCGATGTACG    3180

CGCGCGTGGA TGAAGACCAG CCCTTCCCGG CTGTGCCGAA ATGGTCCATC AAAAAATGGC    3240

TTTCGCTACC TGGAGAGACG CGCCCGCTGA TCCTTTGCGA ATACGCCCAC GCGATGGGTA    3300

ACAGTCTTGG CGGTTTCGCT AAATACTGGC AGGCGTTTCG TCAGTATCCC CGTTTACAGG    3360

GCGGCTTCGT CTGGGACTGG GTGGATCAGT CGCTGATTAA ATATGATGAA AACGGCAACC    3420

CGTGGTCGGC TTACGGCGGT GATTTTGGCG ATACGCCGAA CGATCGCCAG TTCTGTATGA    3480

ACGGTCTGGT CTTTGCCGAC CGCACGCCGC ATCCAGCGCT GACGGAAGCA AAACACCAGC    3540

AGCAGTTTTT CCAGTTCCGT TTATCCGGGC AAACCATCGA AGTGACCAGC GAATACCTGT    3600

TCCGTCATAG CGATAACGAG CTCCTGCACT GGATGGTGGC GCTGGATGGT AAGCCGCTGG    3660

CAAGCGGTGA AGTGCCTCTG GATGTCGCTC CACAAGGTAA ACAGTTGATT GAACTGCCTG    3720

AACTACCGCA GCCGGAGAGC GCCGGGCAAC TCTGGCTCAC AGTACGCGTA GTGCAACCGA    3780
```

```
ACGCGACCGC ATGGTCAGAA GCCGGGCACA TCAGCGCCTG GCAGCAGTGG CGTCTGGCGG    3840

AAAACCTCAG TGTGACGCTC CCCGCCGCGT CCCACGCCAT CCCGCATCTG ACCACCAGCG    3900

AAATGGATTT TTGCATCGAG CTGGGTAATA AGCGTTGGCA ATTTAACCGC CAGTCAGGCT    3960

TTCTTTCACA GATGTGGATT GGCGATAAAA ACAACTGCT GACGCCGCTG CGCGATCAGT    4020

TCACCCGTGC ACCGCTGGAT AACGACATTG GCGTAAGTGA AGCGACCCGC ATTGACCCTA    4080

ACGCCTGGGT CGAACGCTGG AAGGCGGCGG GCCATTACCA GGCCGAAGCA GCGTTGTTGC    4140

AGTGCACGGC AGATACACTT GCTGATGCGG TGCTGATTAC GACCGCTCAC GCGTGGCAGC    4200

ATCAGGGGAA AACCTTATTT ATCAGCCGGA AAACCTACCG GATTGATGGT AGTGGTCAAA    4260

TGGCGATTAC CGTTGATGTT GAAGTGGCGA GCGATACACC GCATCCGGCG CGGATTGGCC    4320

TGAACTGCCA GCTGGCGCAG GTAGCAGAGC GGGTAAACTG GCTCGGATTA GGGCCGCAAG    4380

AAAACTATCC CGACCGCCTT ACTGCCGCCT GTTTTGACCG CTGGGATCTG CCATTGTCAG    4440

ACATGTATAC CCCGTACGTC TTCCCGAGCG AAAACGGTCT GCGCTGCGGG ACGCGCGAAT    4500

TGAATTATGG CCCACACCAG TGGCGCGGCG ACTTCCAGTT CAACATCAGC CGCTACAGTC    4560

AACAGCAACT GATGGAAACC AGCCATCGCC ATCTGCTGCA CGCGGAAGAA GGCACATGGC    4620

TGAATATCGA CGGTTTCCAT ATGGGGATTG GTGGCGACGA CTCCTGGAGC CCGTCAGTAT    4680

CGGCGGAATT GCAGCTGAGC GCCGGTCGCT ACCATTACCA GTTGGTCTGG TGTCAAAAAT    4740

AATAATAACC GGGCAGGCCA TGTCTGCCCG TATTTCGCGT AAGGAAATCC ATTATGTACT    4800

ATTTCTAGAG AATTCCCCCC TCTCCCTCCC CCCCCCCTAA CGTTACTGGC CGAAGCCGCT    4860

TGGAATAAGG CCGGTGTGCG TTTGTCTATA TGTTATTTTC CACCATATTG CCGTCTTTTG    4920

GCAATGTGAG GGCCCGGAAA CCTGGCCCTG TCTTCTTGAC GAGCATTCCT AGGGGTCTTT    4980

CCCCTCTGCG CAAAGGAATG CAAGGTCTGT TGAATGTCGT GAAGGAAGCA GTTCCTCTGG    5040

AAGCTTCTTG AAGACAAACA ACGTCTGTAG CGACCCTTTG CAGGCAGCGG AACCCCCCAC    5100

CTGGCGACAG GTGCCTCTGC GGCCAAAAGC CACGTGTATA AGATACACCT GCAAAGGCGG    5160

CACAACCCCA GTGCCACGTT GTGAGTTGGA TAGTTGTGGA AAGAGTCAAA TGGCTCTCCT    5220

CAAGCGTATT CAACAAGGGG CTGAAGGATG CCCAGAAGGT ACCCCATTGT ATGGGATCTG    5280

ATCTGGGGCC TCGGTGCACA TGCTTTACAT GTGTTTAGTC GAGGTTAAAA AACGTCTAGG    5340

CCCCCCGAAC CACGGGGACG TGGTTTTCCT TTGAAAAACA CGATGATAAT ATGGCCAAGC    5400

TCCTAGGCTT TTGCAAAAAG CTCCCGGGAG CTTGGATATC CATTTTCGGA TCTGATCAAG    5460

AGACAGGATG AGGATCGTTT CGCATGATTG AACAAGATGG ATTGCACGCA GGTTCTCCGG    5520

CCGCTTGGGT GGAGAGGCTA TTCGGCTATG ACTGGGCACA ACAGACAATC GGCTGCTCTG    5580

ATGCCGCCGT GTTCCGGCTG TCAGCGCAGG GGCGCCCGGT TCTTTTTGTC AAGACCGACC    5640

TGTCCGGTGC CCTGAATGAA CTGCAGGACG AGGCAGCGCG GCTATCGTGG CTGGCCACGA    5700

CGGGCGTTCC TTGCGCAGCT GTGCTCGACG TTGTCACTGA AGCGGGAAGG GACTGGCTGC    5760

TATTGGGCGA AGTGCCGGGG CAGGATCTCC TGTCATCTCA CCTTGCTCCT GCCGAGAAAG    5820

TATCCATCAT GGCTGATGCA ATGCGGCGGC TGCATACGCT TGATCCGGCT ACCTGCCCAT    5880

TCGACCACCA AGCGAAACAT CGCATCGAGC GAGCACGTAC TCGGATGGAA GCCGGTCTTG    5940

TCGATCAGGA TGATCTGGAC GAAGAGCATC AGGGGCTCGC GCCAGCCGAA CTGTTCGCCA    6000

GGCTCAAGGC GCGCATGCCC GACGGCGAGG ATCTCGTCGT GACCCATGGC GATGCCTGCT    6060

TGCCGAATAT CATGGTGGAA AATGGCCGCT TTTCTGGATT CATCGACTGT GGCCGGCTGG    6120
```

```
GTGTGGCGGA CCGCTATCAG GACATAGCGT TGGCTACCCG TGATATTGCT GAAGAGCTTG      6180

GCGGCGAATG GGCTGACCGC TTCCTCGTGC TTTACGGTAT CGCCGCTCCC GATTCGCAGC      6240

GCATCGCCTT CTATCGCCTT CTTGACGAGT TCTTCTGAGC GGGACTCTGG GGTTCGCCTT      6300

GACTTGCTGT TTCTAAAAGA AGGTGGCCTC TGTGCGGCCC TAAAGGAAGA GTGCTGTTTT      6360

TACATAGACC ACTCAGGTGC AGTACGGGAC TCCATGAAAA AACTCAAAGA AAAACTGGAT      6420

AAAAGACAGT TAGAGCGCCA GAAAAGCCAA ACTGGTATG AAGGATGGTT CAATAACTCC       6480

CCTTGGTTCA CTACCCTGCT ATCAACCATC GCTGGGCCCC TATTACTCCT CCTTCTGTTG      6540

CTCATCCTCG GGCCATGCAT CAATAAGTTA GTTCAATTCA TCAATGATAG GATAAGTGCA     6600

TGTTAAAATT CTGGTCCTTA GACAAAATAT CAGGCCCTAG AGAACGAAGG TAACCTTTAA      6660

TTTTGCTCTA AGATTAGAGC TATTCACAAG AGAAATGGGG GAATGAAAGA AGTGTTTTTT     6720

TTTAGCCAAC TGCAGTAACG CCATTTTGCT AGGCACACCT AAAGGATAGG AAAAATACAG      6780

CTAAGAACAG GGCCAAACAG GATATCTGTG GTCATGCACC TGGGCCCCGG CCCAGGCCAA      6840

GGACAGAGGG TTCCCAGAAA TAGATGAGTC AACAGCAGTT TCCAGCAAGG ACAGAGGGTT      6900

CCCAGAAATA GATGAGTCAA CAGCAGTTTC CAGCAAGGAC AGAGGGTTCC CAGAAATAGA     6960

TGAGTCAACA GCAGTTTCCA GGGTGCCCCT CAACCGTTTC AAGGACTCCC ATGACCGGGA     7020

ATTCACCCCT GGCCTTATTT GAACTAACCA ATTACCTTGC CTCTCGCTTC TGTACCCGCG     7080

CTTTTTGCTA TAAAATAAGC TCAGAAACTC CACCCGGAGC GCCAGTCCTT AGAGAGACTG     7140

AGCCGCCCGG GTACCCGTGT GATCAATAAA ACCTCTTGCT ACTTGCATCC GAAGTCGTGG     7200

TCTCGCTGTT CCTTGGGAAG GTCTCCCCTA ATTGATTGAC CGCCCGGACT GGGGGTCTCT     7260

CATTGGAATT CATCGATGAT ATCAGATCTG CCGGTCTCCC TATAGTGAGT CGTATTAATT     7320

TCGATAAGCC AGGTTAACCT GCATTAATGA ATCGGCCAAC GCGCGGGGAG AGGCGGTTTG     7380

CGTATTGGGC GCTCTTCCGC TTCCTCGCTC ACTGACTCGC TGCGCTCGGT CGTTCGGCTG     7440

CGGCGAGCGG TATCAGCTCA CTCAAAGGCG GTAATACGGT TATCCACAGA ATCAGGGGAT     7500

AACGCAGGAA AGAACATGTG AGCAAAAGGC CAGCAAAAGG CCAGGAACCG TAAAAAGGCC     7560

GCGTTGCTGG CGTTTTTCCA TAGGCTCCGC CCCCCTGACG AGCATCACAA AAATCGACGC     7620

TCAAGTCAGA GGTGGCGAAA CCCGACAGGA CTATAAAGAT ACCAGGCGTT TCCCCCTGGA     7680

AGCTCCCTCG TGCGCTCTCC TGTTCCGACC CTGCCGCTTA CCGGATACCT GTCCGCCTTT     7740

CTCCCTTCGG GAAGCGTGGC GCTTTCTCAA TGCTCACGCT GTAGGTATCT CAGTTCGGTG     7800

TAGGTCGTTC GCTCCAAGCT GGGCTGTGTG CACGAACCCC CCGTTCAGCC CGACCGCTGC     7860

GCCTTATCCG GTAACTATCG TCTTGAGTCC AACCCGGTAA GACACGACTT ATCGCCACTG     7920

GCAGCAGCCA CTGGTAACAG GATTAGCAGA GCGAGGTATG TAGGCGGTGC TACAGAGTTC     7980

TTGAAGTGGT GGCCTAACTA CGGCTACACT AGAAGGACAG TATTTGGTAT CTGCGCTCTG     8040

CTGAAGCCAG TTACCTTCGG AAAAAGAGTT GGTAGCTCTT GATCCGGCAA ACAAACCACC     8100

GCTGGTAGCG GTGGTTTTTT TGTTTGCAAG CAGCAGATTA CGCGCAGAAA AAAAGGATCT     8160

CAAGAAGATC CTTTGATCTT TTCTACGGGG TCTGACGCTC AGTGGAACGA AAACTCACGT     8220

TAAGGGATTT TGGTCATGAG ATTATCAAAA AGGATCTTCA CCTAGATCCT TTTAAATTAA     8280

AAATGAAGTT TTAAATCAAT CTAAAGTATA TATGAGTAAA CTTGGTCTGA CAGTTACCAA     8340

TGCTTAATCA GTGAGGCACC TATCTCAGCG ATCTGTCTAT TTCGTTCATC CATAGTTGCC     8400

TGACTCCCCG TCGTGTAGAT AACTACGATA CGGGAGGGCT TACCATCTGG CCCCAGTGCT     8460

GCAATGATAC CGCGAGACCC ACGCTCACCG GCTCCAGATT TATCAGCAAT AAACCAGCCA     8520
```

-continued

```
GCCGGAAGGG CCGAGCGCAG AAGTGGTCCT GCAACTTTAT CCGCCTCCAT CCAGTCTATT      8580

AATTGTTGCC GGGAAGCTAG AGTAAGTAGT TCGCCAGTTA ATAGTTTGCG CAACGTTGTT      8640

GCCATTGCTA CAGGCATCGT GGTGTCACGC TCGTCGTTTG GTATGGCTTC ATTCAGCTCC      8700

GGTTCCCAAC GATCAAGGCG AGTTACATGA TCCCCCATGT TGTGCAAAAA AGCGGTTAGC      8760

TCCTTCGGTC CTCCGATCGT TGTCAGAAGT AAGTTGGCCG CAGTGTTATC ACTCATGGTT      8820

ATGGCAGCAC TGCATAATTC TCTTACTGTC ATGCCATCCG TAAGATGCTT TTCTGTGACT      8880

GGTGAGTACT CAACCAAGTC ATTCTGAGAA TAGTGTATGC GGCGACCGAG TTGCTCTTGC      8940

CCGGCGTCAA TACGGGATAA TACCGCGCCA CATAGCAGAA CTTTAAAAGT GCTCATCATT      9000

GGAAAACGTT CTTCGGGGCG AAAACTCTCA AGGATCTTAC CGCTGTTGAG ATCCAGTTCG      9060

ATGTAACCCA CTCGTGCACC CAACTGATCT TCAGCATCTT TTACTTTCAC CAGCGTTTCT      9120

GGGTGAGCAA AAACAGGAAG GCAAAATGCC GCAAAAAAGG GAATAAGGGC GACACGGAAA      9180

TGTTGAATAC TCATACTCTT CCTTTTTCAA TATTATTGAA GCATTTATCA GGGTTATTGT      9240

CTCATGAGCG GATACATATT TGAATGTATT TAGAAAAATA AACAAATAGG GGTTCCGCGC      9300

ACATTTCCCC GAAAAGTGCC ACCTGACGTC TAAGAAACCA TTATTATCAT GACATTAACC      9360

TATAAAAATA GGCGTATCAC GAGGCCCTTT CGTCTCGCGC GTTTCGGTGA TGACGGTGAA      9420

AACCTCTGAC ACATGCAGCT CCCGGAGACG GTCACAGCTT GTCTGTAAGC GGATGCCGGG      9480

AGCAGACAAG CCCGTCAGGG CGCGTCAGCG GGTGTTGGCG GGTGTCGGGG CTGGCTTAAC      9540

TATGCGGCAT CAGAGCAGAT TGTACTGAGA GTGCACCATA TGGACATATT GTCGTTAGAA      9600

CGCGGCTACA ATTAATACAT AACCTTATGT ATCATACACA TACGATTTAG GTGACACTAT      9660

A                                                                     9661
```

(2) INFORMATION FOR SEQ ID NO:4:

(i) SEQUENCE CHARACTERISTICS:
        (A) LENGTH: 10306 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..10258
        (D) OTHER INFORMATION: /standard_name= "p521 retroviral
            vector"

(xi) SEQUENCE DESCRIPTION: SEQ ID NO:4:

```
AAGCTTCGGC CAAGTGCGGC CCTTCCGTTT CTTTGCTTTT GAAAGACCCC ACCCGTAGGT        60

GGCAAGCTAG CTTAAGTAAC GCCACTTTGC AAGGCATGGA AAAATACATA ACTGAGAATA       120

GGAAAGTTCA GATCAAGGTC AGGAACAAAG AAACAGCTGA ATACCAAACA GGATATCTGT       180

GGTAAGCGGT TCCTGCCCCC GGCTCAGGGC CAAGAACAGA TGAGACAGCT GAGTGATGGG       240

CCAAACAGGA TATCTGTGGT AAGCAGTTCC TGCCCCGGCT CGGGGCCAAG AACAGATGGT       300

CCCCAGATGC GGTCCAGCCC TCAGCAGTTT CTAGTGAATC ATCAGATGTT TCCAGGGTGC       360

CCCAAGGACC TGAAAATGAC CCTGTACCTT ATTTGAACTA ACCAATCAGT TCGCTTCTCG       420

CTTCTGTTCG CGCGCTTCCG CTCTCCGAGC TCAATAAAAG AGCCCACAAC CCCTCACTCG       480

GCGCGCCAGT CTTCCGATAG ACTGCGTCGC CCGGGTACCC GTATTCCCAA TAAAGCCTCT       540

TGCTGTTTGC ATCCGAATCG TGGTCTCGCT GTTCCTTGGG AGGGTCTCCT CTGAGTGATT       600
```

```
GACTACCCAC GACGGGGTC TTTCATTTGG GGGCTCGTCC GGGATTTGGA GACCCCTGCC    660

CAGGGACCAC CGACCCACCA CCGGGAGGTA AGCTGGCCAG CAACCTATCT GTGTCTGTCC    720

GATTGTCTAG TGTCTATGTT TGATGTTATG CGCCTGCGTC TGTACTAGTT AGCTAACTAG    780

CTCTGTATCT GGCGGACCCG TGGTGGAACT GACGAGTTCT GAACACCCGG CCGCAACCCA    840

GGGAGACGTC CCAGGGACTT TGGGGGCCGT TTTTGTGGCC CGACCTGAGG AAGGGAGTCG    900

ATGTGGAATC CGACCCCGTC AGGATATGTG GTTCTGGTAG GAGACGAGAA CCTAAAACAG    960

TTCCCGCCTC CGTCTGAATT TTTGCTTTCG GTTTGGAACC GAAGCCGCGC GTCTTGTCTG   1020

CTGCAGCATC GTTCTGTGTT GTCTCTGTCT GACTGTGTTT CTGTATTTGT CTGAAAATTA   1080

GGGCCAGACT GTTACCACTC CCTTAAGTTT GACCTTAGGT CACTGGAAAG ATGTCGAGCG   1140

GATCGCTCAC AACCAGTCGG TAGATGTCAA GAAGAGACGT TGGGTTACCT TCTGCTCTGC   1200

AGAATGGCCA ACCTTTACGT CGGATGGCCG CGAGACGGCA CCTTTAACCG AGACCTCATC   1260

ACCCAGGTTA AGATCAAGGT CTTTTCACCT GGCCCGCATG GACACCCAGA CCAGGTCCCC   1320

TACATCGTGA CCTGGGAAGC CTTGGCTTTT GACCCCCCTC CCTGGGTCAA GCCCTTTGTA   1380

CACCCTAAGC CTCCGCCTCC TCTTCCTCCA TCCGCCCCGT CTCTCCCCCT TGAACCTCCT   1440

CGTTCGACCC CGCCTCGATC CTCCCTTTAT CCAGCCCTCA CTCCTTCTCT AGGCGGGAAT   1500

TCGTTAACTC GACCCGCGGG TCGACTCGCG AAGATCTTTC CGCAGCAGCC GCCACCATGG   1560

TTACGGATTC GGATCCCGTC GTTTTACAAC GTCGTGACTG GGAAAACCCT GGCGTTACCC   1620

AACTTAATCG CCTTGCAGCA CATCCCCCTT TCGCCAGCTG GCGTAATAGC GAAGAGGCCC   1680

GCACCGATCG CCCTTCCCAA CAGTTGCGCA GCCTGAATGG CGAATGGCGC TTTGCCTGGT   1740

TTCCGGCACC AGAAGCGGTG CCGGAAAGCT GGCTGGAGTG CGATCTTCCT GAGGCCGATA   1800

CTGTCGTCGT CCCCTCAAAC TGGCAGATGC ACGGTTACGA TGCGCCCATC TACACCAACG   1860

TAACCTATCC CATTACGGTC AATCCGCCGT TTGTTCCCAC GGAGAATCCG ACGGGTTGTT   1920

ACTCGCTCAC ATTTAATGTT GATGAAAGCT GGCTACAGGA AGGCCAGACG CGAATTATTT   1980

TTGATGGCGT TAACTCGGCG TTTCATCTGT GGTGCAACGG GCGCTGGGTC GGTTACGGCC   2040

AGGACAGTCG TTTGCCGTCT GAATTTGACC TGAGCGCATT TTTACGCGCC GGAGAAAACC   2100

GCCTCGCGGT GATGGTGCTG CGTTGGAGTG ACGGCAGTTA TCTGGAAGAT CAGGATATGT   2160

GGCGGATGAG CGGCATTTTC CGTGACGTCT CGTTGCTGCA TAAACCGACT ACACAAATCA   2220

GCGATTTCCA TGTTGCCACT CGCTTTAATG ATGATTTCAG CCGCGCTGTA CTGGAGGCTG   2280

AAGTTCAGAT GTGCGGCGAG TTGCGTGACT ACCTACGGGT AACAGTTTCT TTATGGCAGG   2340

GTGAAACGCA GGTCGCCAGC GGCACCGCGC CTTTCGGCGG TGAAATTATC GATGAGCGTG   2400

GTGGTTATGC CGATCGCGTC ACACTACGTC TGAACGTCGA AAACCCGAAA CTGTGGAGCG   2460

CCGAAATCCC GAATCTCTAT CGTGCGGTGG TTGAACTGCA CACCGCCGAC GGCACGCTGA   2520

TTGAAGCAGA AGCCTGCGAT GTCGGTTTCC GCGAGGTGCG GATTGAAAAT GGTCTGCTGC   2580

TGCTGAACGG CAAGCCGTTG CTGATTCGAG GCGTTAACCG TCACGAGCAT CATCCTCTGC   2640

ATGGTCAGGT CATGGATGAG CAGACGATGG TGCAGGATAT CCTGCTGATG AAGCAGAACA   2700

ACTTTAACGC CGTGCGCTGT TCGCATTATC CGAACCATCC GCTGTGGTAC ACGCTGTGCG   2760

ACCGCTACGG CCTGTATGTG GTGGATGAAG CCAATATTGA AACCCACGGC ATGGTGCCAA   2820

TGAATCGTCT GACCGATGAT CCGCGCTGGC TACCGGCGAT GAGCGAACGC GTAACGCGAA   2880

TGGTGCAGCG CGATCGTAAT CACCCGAGTG TGATCATCTG GTCGCTGGGG AATGAATCAG   2940
```

```
GCCACGGCGC TAATCACGAC GCGCTGTATC GCTGGATCAA ATCTGTCGAT CCTTCCCGCC    3000

CGGTGCAGTA TGAAGGCGGC GGAGCCGACA CCACGGCCAC CGATATTATT TGCCCGATGT    3060

ACGCGCGCGT GGATGAAGAC CAGCCCTTCC CGGCTGTGCC GAAATGGTCC ATCAAAAAAT    3120

GGCTTTCGCT ACCTGGAGAG ACGCGCCCGC TGATCCTTTG CGAATACGCC CACGCGATGG    3180

GTAACAGTCT TGGCGGTTTC GCTAAATACT GGCAGGCGTT TCGTCAGTAT CCCCGTTTAC    3240

AGGGCGGCTT CGTCTGGGAC TGGGTGGATC AGTCGCTGAT TAAATATGAT GAAAACGGCA    3300

ACCCGTGGTC GGCTTACGGC GGTGATTTTG GCGATACGCC GAACGATCGC CAGTTCTGTA    3360

TGAACGGTCT GGTCTTTGCC GACCGCACGC CGCATCCAGC GCTGACGGAA GCAAACACC    3420

AGCAGCAGTT TTTCCAGTTC CGTTTATCCG GGCAAACCAT CGAAGTGACC AGCGAATACC    3480

TGTTCCGTCA TAGCGATAAC GAGCTCCTGC ACTGGATGGT GGCGCTGGAT GGTAAGCCGC    3540

TGGCAAGCGG TGAAGTGCCT CTGGATGTCG CTCCACAAGG TAAACAGTTG ATTGAACTGC    3600

CTGAACTACC GCAGCCGGAG AGCGCCGGGC AACTCTGGCT CACAGTACGC GTAGTGCAAC    3660

CGAACGCGAC CGCATGGTCA GAAGCCGGGC ACATCAGCGC CTGGCAGCAG TGGCGTCTGG    3720

CGGAAAACCT CAGTGTGACG CTCCCCGCCG CGTCCCACGC CATCCCGCAT CTGACCACCA    3780

GCGAAATGGA TTTTTGCATC GAGCTGGGTA ATAAGCGTTG GCAATTTAAC CGCCAGTCAG    3840

GCTTTCTTTC ACAGATGTGG ATTGGCGATA AAAACAACT GCTGACGCCG CTGCGCGATC    3900

AGTTCACCCG TGCACCGCTG GATAACGACA TTGGCGTAAG TGAAGCGACC CGCATTGACC    3960

CTAACGCCTG GGTCGAACGC TGGAAGGCGG CGGGCCATTA CCAGGCCGAA GCAGCGTTGT    4020

TGCAGTGCAC GGCAGATACA CTTGCTGATG CGGTGCTGAT TACGACCGCT CACGCGTGGC    4080

AGCATCAGGG GAAAACCTTA TTTATCAGCC GGAAAACCTA CCGGATTGAT GGTAGTGGTC    4140

AAATGGCGAT TACCGTTGAT GTTGAAGTGG CGAGCGATAC ACCGCATCCG GCGCGGATTG    4200

GCCTGAACTG CCAGCTGGCG CAGGTAGCAG AGCGGGTAAA CTGGCTCGGA TTAGGGCCGC    4260

AAGAAAACTA TCCCGACCGC CTTACTGCCG CCTGTTTTGA CCGCTGGGAT CTGCCATTGT    4320

CAGACATGTA TACCCCGTAC GTCTTCCCGA GCGAAAACGG TCTGCGCTGC GGGACGCGCG    4380

AATTGAATTA TGGCCCACAC CAGTGGCGCG GCGACTTCCA GTTCAACATC AGCCGCTACA    4440

GTCAACAGCA ACTGATGGAA ACCAGCCATC GCCATCTGCT GCACGCGGAA GAAGGCACAT    4500

GGCTGAATAT CGACGGTTTC CATATGGGGA TTGGTGGCGA CGACTCCTGG AGCCCGTCAG    4560

TATCGGCGGA ATTGCAGCTG AGCGCCGGTC GCTACCATTA CCAGTTGGTC TGGTGTCAAA    4620

AATAATAATA ACCGGGCAGG CCATGTCTGC CCGTATTTCG CGTAAGGAAA TCCATTATGT    4680

ACTATTTCTA GAGAATTCCC CCCTCTCCCT CCCCCCCCCC TAACGTTACT GGCCGAAGCC    4740

GCTTGGAATA AGGCCGGTGT GCGTTTGTCT ATATGTTATT TTCCACCATA TTGCCGTCTT    4800

TTGGCAATGT GAGGGCCCGG AAACCTGGCC CTGTCTTCTT GACGAGCATT CCTAGGGGTC    4860

TTTCCCCTCT GCGCAAAGGA ATGCAAGGTC TGTTGAATGT CGTGAAGGAA GCAGTTCCTC    4920

TGGAAGCTTC TTGAAGACAA ACAACGTCTG TAGCGACCCT TTGCAGGCAG CGGAACCCCC    4980

CACCTGGCGA CAGGTGCCTC TGCGGCCAAA AGCCACGTGT ATAAGATACA CCTGCAAAGG    5040

CGGCACAACC CCAGTGCCAC GTTGTGAGTT GGATAGTTGT GGAAAGAGTC AAATGGCTCT    5100

CCTCAAGCGT ATTCAACAAG GGGCTGAAGG ATGCCCAGAA GGTACCCCAT TGTATGGGAT    5160

CTGATCTGGG GCCTCGGTGC ACATGCTTTA CATGTGTTTA GTCGAGGTTA AAAAACGTCT    5220

AGGCCCCCCG AACCACGGGG ACGTGGTTTT CCTTTGAAAA ACACGATGAT AATATGGCCA    5280

AGCTCCTAGG CTTTTGCAAA AAGCTCCCGG GAGCTTGGAT ATCCATTTTC GGATCTGATC    5340
```

```
AAGAGACAGG ATGAGGATCG TTTCGCATGA TTGAACAAGA TGGATTGCAC GCAGGTTCTC        5400

CGGCCGCTTG GGTGGAGAGG CTATTCGGCT ATGACTGGGC ACAACAGACA ATCGGCTGCT        5460

CTGATGCCGC CGTGTTCCGG CTGTCAGCGC AGGGGCGCCC GGTTCTTTTT GTCAAGACCG        5520

ACCTGTCCGG TGCCCTGAAT GAACTGCAGG ACGAGGCAGC GCGGCTATCG TGGCTGGCCA        5580

CGACGGGCGT TCCTTGCGCA GCTGTGCTCG ACGTTGTCAC TGAAGCGGGA AGGGACTGGC        5640

TGCTATTGGG CGAAGTGCCG GGGCAGGATC TCCTGTCATC TCACCTTGCT CCTGCCGAGA        5700

AAGTATCCAT CATGGCTGAT GCAATGCGGC GGCTGCATAC GCTTGATCCG GCTACCTGCC        5760

CATTCGACCA CCAAGCGAAA CATCGCATCG AGCGAGCACG TACTCGGATG GAAGCCGGTC        5820

TTGTCGATCA GGATGATCTG GACGAAGAGC ATCAGGGGCT CGCGCCAGCC GAACTGTTCG        5880

CCAGGCTCAA GGCGCGCATG CCCGACGGCG AGGATCTCGT CGTGACCCAT GGCGATGCCT        5940

GCTTGCCGAA TATCATGGTG GAAAATGGCC GCTTTTCTGG ATTCATCGAC TGTGGCCGGC        6000

TGGGTGTGGC GGACCGCTAT CAGGACATAG CGTTGGCTAC CCGTGATATT GCTGAAGAGC        6060

TTGGCGGCGA ATGGGCTGAC CGCTTCCTCG TGCTTTACGG TATCGCCGCT CCCGATTCGC        6120

AGCGCATCGC CTTCTATCGC CTTCTTGACG AGTTCTTCTG AGCGGGACTC TGGGGTTCGC        6180

CTTGACTTGC TGTTTCTAAA AGAAGGTGGC CTCTGTGCGG CCCTAAAGGA AGAGTGCTGT        6240

TTTTACATAG ACCACTCAGG TGCAGTACGG GACTCCATGA AAAAACTCAA AGAAAAACTG        6300

GATAAAAGAC AGTTAGAGCG CCAGAAAAGC CAAAACTGGT ATGAAGGATG GTTCAATAAC        6360

TCCCCTTGGT TCACTACCCT GCTATCAACC ATCGCTGGGC CCTATTACT CCTCCTTCTG        6420

TTGCTCATCC TCGGGCCATG CATCATCAAT AAGTTAGTTC AATTCATCAA TGATAGGATA        6480

AGTGCATGTT AAAATTCTGG TCCTTAGACA AAATATCAGG CCCTAGAGAA CGAAGGTAAC        6540

CTTTAATTTT GCTCTAAGAT TAGAGCTATT CACAAGAGAA ATGGGGGAAT GAAAGAAGTG        6600

TTTTTTTTTA GCCAACTGCA GTAACGCCAT TTTGCTAGGC ACACCTAAAG GATAGGAAAA        6660

ATACAGCTAA GAACAGGGCC AAACAGGATA TCTGTGGTCA TGCACCTGGG CCCCGGCCCA        6720

GGCCAAGGAC AGAGGGTTCC CAGAAATAGA TGAGTCAACA GCAGTTTCCA GCAAGGACAG        6780

AGGGTTCCCA GAAATAGATG AGTCAACAGC AGTTTCCAGC AAGGACAGAG GGTTCCCAGA        6840

AATAGATGAG TCAACAGCAG TTTCCAGGGT GCCCCTCAAC CGTTTCAAGG ACTCCCATGA        6900

CCGGGAATTC ACCCCTGGCC TTATTTGAAC TAACCAATTA CCTTGCCTCT CGCTTCTGTA        6960

CCCGCGCTTT TTGCTATAAA ATAAGCTCAG AAACTCCACC CGGAGCGCCA GTCCTTAGAG        7020

AGACTGAGCC GCCCGGGTAC CCGTGTGTCC AATAAAACCT CTTGCTGATT GCATCCGGAG        7080

CCGTGGTCTC GTTGTTCCTT GGGAGGGTTT CTCCTAACTA TTGACCGCCC ACTTCGGGGG        7140

TCTCACATTT GCGGCCGCCA ATTCGCCCTA TAGTGAGTCG TATTACAATT CACTGGCCGT        7200

CGTTTTACAA CGTCGTGACT GGGAAAACCC TGGCGTTACC CAACTTAATC GCCTTGCAGC        7260

ACATCCCCCT TTCGCCAGCT GGCGTAATAG CGAAGAGGCC CGCACCGATC GCCCTTCCCA        7320

ACAGTTGCGC AGCCTGAATG GCGAATGGAA ATTGTAAACG TTAATATTTT GTTAAAATTC        7380

GCGTTAAATA TTTGTTAAAT CAGCTCATTT TTTAACCAAT AGGCCGAAAT CGGCAAAATC        7440

CCTTATAAAT CAAAAGAATA GACCGAGATA GGGTTGAGTG TTGTTCCAGT TTGGAACAAG        7500

AGTCCACTAT TAAAGAACGT GGACTCCAAC GTCAAAGGGC GAAAAACCGT CTATCAGGGC        7560

GATGGCCCAC TACGTGAACC ATCACCCAAA TCAAGTTTTT TGCGGTCGAG GTGCCGTAAA        7620

GCTCTAAATC GGAACCCTAA AGGGAGCCCC CGATTTAGAG CTTGACGGGG AAAGCCGGCG        7680
```

```
AACGTGGCGA GAAAGGAAGG GAAGAAAGCG AAAGGAGCGG GCGCTAGGGC GCTGGCAAGT     7740

GTAGCGGTCA CGCTGCGCGT AACCACCACA CCCGCCGCGC TTAATGCGCC GCTACAGGGC     7800

GCGTCGCCTG ATGCGGTATT TTCTCCTTAC GCATCTGTGC GGTATTTCAC ACCGCATATG     7860

GTGCACTCTC AGTACAATCT GCTCTGATGC CGCATAGTTA AGCCAGCCCC GACACCCGCC     7920

AACACCCGCT GACGCGCCCT GACGGGCTTG TCTGCTCCCG GCATCCGCTT ACAGACAAGC     7980

TGTGACCGTC TCCGGGAGCT GCATGTGTCA GAGGTTTTCA CCGTCATCAC CGAAACGCGC     8040

GAGACGAAAG GGCCTCGTGA TACGCCTATT TTTATAGGTT AATGTCATGA TAATAATGGT     8100

TTCTTAGACG TCAGGTGGCA CTTTTCGGGG AAATGTGCGC GGAACCCCTA TTTGTTTATT     8160

TTTCTAAATA CATTCAAATA TGTATCCGCT CATGAGACAA TAACCCTGAT AAATGCTTCA     8220

ATAATATTGA AAAAGGAAGA GTATGAGTAT TCAACATTTC CGTGTCGCCC TTATTCCCTT     8280

TTTTGCGGCA TTTTGCCTTC CTGTTTTTGC TCACCCAGAA ACGCTGGTGA AAGTAAAAGA     8340

TGCTGAAGAT CAGTTGGGTG CACGAGTGGG TTACATCGAA CTGGATCTCA ACAGCGGTAA     8400

GATCCTTGAG AGTTTTCGCC CCGAAGAACG TTTTCCAATG ATGAGCACTT TTAAAGTTCT     8460

GCTATGTCAT ACACTATTAT CCCGTATTGA CGCCGGGCAA GAGCAACTCG GTCGCCGGGC     8520

GCGGTATTCT CAGAATGACT TGGTTGAGTA CTCACCAGTC ACAGAAAAGC ATCTTACGGA     8580

TGGCATGACA GTAAGAGAAT TATGCAGTGC TGCCATAACC ATGAGTGATA ACACTGCGGC     8640

CAACTTACTT CTGACAACGA TCGGAGGACC GAAGGAGCTA ACCGCTTTTT TGCACAACAT     8700

GGGGGATCAT GTAACTCGCC TTGATCGTTG GGAACCGGAG CTGAATGAAG CCATACCAAA     8760

CGACGAGCGT GACACCACGA TGCCTGTAGC AATGCCAACA ACGTTGCGCA AACTATTAAC     8820

TGGCGAACTA CTTACTCTAG CTTCCCGGCA ACAATTAATA GACTGGATGG AGGCGGATAA     8880

AGTTGCAGGA CCACTTCTGC GCTCGGCCCT TCCGGCTGGC TGGTTTATTG CTGATAAATC     8940

TGGAGCCGGT GAGCGTGGGT CTCGCGGTAT CATTGCAGCA CTGGGGCCAG ATGGTAAGCC     9000

CTCCCGTATC GTAGTTATCT ACACGACGGG GAGTCAGGCA ACTATGGATG AACGAAATAG     9060

ACAGATCGCT GAGATAGGTG CCTCACTGAT TAAGCATTGG TAACTGTCAG ACCAAGTTTA     9120

CTCATATATA CTTTAGATTG ATTTAAAACT TCATTTTTAA TTTAAAAGGA TCTAGGTGAA     9180

GATCCTTTTT GATAATCTCA TGACCAAAAT CCCTTAACGT GAGTTTTCGT TCCACTGAGC     9240

GTCAGACCCC GTAGAAAAGA TCAAAGGATC TTCTTGAGAT CCTTTTTTTC TGCGCGTAAT     9300

CTGCTGCTTG CAAACAAAAA AACCACCGCT ACCAGCGGTG GTTTGTTTGC CGGATCAAGA     9360

GCTACCAACT CTTTTTCCGA AGGTAACTGG CTTCAGCAGA GCGCAGATAC CAAATACTGT     9420

CCTTCTAGTG TAGCCGTAGT TAGGCCACCA CTTCAAGAAC TCTGTAGCAC CGCCTACATA     9480

CCTCGCTCTG CTAATCCTGT TACCAGTGGC TGCTGCCAGT GGCGATAAGT CGTGTCTTAC     9540

CGGGTTGGAC TCAAGACGAT AGTTACCGGA TAAGGCGCAG CGGTCGGGCT GAACGGGGGG     9600

TTCGTGCACA CAGCCCAGCT TGGAGCGAAC GACCTACACC GAACTGAGAT ACCTACAGCG     9660

TGAGCTATGA GAAAGCGCCA CGCTTCCCGA AGGGAGAAAG GCGGACAGGT ATCCGGTAAG     9720

CGGCAGGGTC GGAACAGGAG AGCGCACGAG GGAGCTTCCA GGGGGAAACG CCTGGTATCT     9780

TTATAGTCCT GTCGGGTTTC GCCACCTCTG ACTTGAGCGT CGATTTTTGT GATGCTCGTC     9840

AGGGGGGCGG AGCCTATCGA AAAACGCCAG CAACGCGGCC TTTTTACGGT TCCTGGCCTT     9900

TTGCTGGCCT TTTGCTCACA TGTTCTTTCC TGCGTTATCC CCTGATTCTG TGGATAACCG     9960

TATTACCGCC TTTGAGTGAG CTGATACCGC TCGCCGCAGC CGAACGACCG AGCGCAGCGA    10020

GTCAGTGAGC GAGGAAGCGG AAGAGCGCCC AATACGCAAA CCGCCTCTCC CCGCGCGTTG    10080
```

```
GCCGATTCAT TAATGCAGCT GGCACGACAG GTTTCCCGAC TGGAAAGCGG GCAGTGAGCG      10140

CAACGCAATT AATGTGAGTT AGCTCACTCA TTAGGCACCC CAGGCTTTAC ACTTTATGCT      10200

TCCGGCTCGT ATGTTGTGTG GAATTGTGAG CGGATAACAA TTTCACACAG GAAACAGCTA     10260

TGACCATGAT TACGCCAAGC TATTTAGGTG ACACTATAGA ATACTC                    10306
```

(2) INFORMATION FOR SEQ ID NO:5:

(i) SEQUENCE CHARACTERISTICS:
        (A) LENGTH: 10970 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..10970
        (D) OTHER INFORMATION: /standard_name= "p537 retroviral
            vector"

(xi) SEQUENCE DESCRIPTION: SEQ ID NO:5:

```
AAGCTTCGGC CAAGTGCGGC CCTTCCGTTT CTTTGCTTTT GAAAGACCCC ACCCGTAGGT        60

GGCAAGCTAG CTTAAGTAAC GCCACTTTGC AAGGCATGGA AAAATACATA ACTGAGAATA       120

GGAAAGTTCA GATCAAGGTC AGGAACAAAG AAACAGCTGA ATACCAAACA GGATATCTGT       180

GGTAAGCGGT TCCTGCCCCC GGCTCAGGGC CAAGAACAGA TGAGACAGCT GAGTGATGGG       240

CCAAACAGGA TATCTGTGGT AAGCAGTTCC TGCCCCGGCT CGGGGCCAAG AACAGATGGT       300

CCCCAGATGC GGTCCAGCCC TCAGCAGTTT CTAGTGAATC ATCAGATGTT TCCAGGGTGC       360

CCCAAGGACC TGAAAATGAC CCTGTACCTT ATTTGAACTA ACCAATCAGT TCGCTTCTCG       420

CTTCTGTTCG CGCGCTTCCG CTCTCCGAGC TCAATAAAAG AGCCCACAAC CCCTCACTCG       480

GCGCGCCAGT CTTCCGATAG ACTGCGTCGC CCGGGTACCC GTATTCCCAA TAAAGCCTCT       540

TGCTGTTTGC ATCCGAATCG TGGTCTCGCT GTTCCTTGGG AGGGTCTCCT CTGAGTGATT       600

GACTACCCAC GACGGGGGTC TTTCATTTGG GGGCTCGTCC GGGATTTGGA GACCCCTGCC       660

CAGGGACCAC CGACCCACCA CCGGGAGGTA AGCTGGCCAG CAACCTATCT GTGTCTGTCC       720

GATTGTCTAG TGTCTATGTT TGATGTTATG CGCCTGCGTC TGTACTAGTT AGCTAACTAG       780

CTCTGTATCT GGCGGACCCG TGGTGGAACT GACGAGTTCT GAACACCCGG CCGCAACCCA       840

GGGAGACGTC CCAGGGACTT TGGGGGCCGT TTTTGTGGCC CGACCTGAGG AAGGGAGTCG       900

ATGTGGAATC CGACCCCGTC AGGATATGTG GTTCTGGTAG GAGACGAGAA CCTAAAACAG       960

TTCCCGCCTC CGTCTGAATT TTTGCTTTCG GTTTGGAACC GAAGCCGCGC GTCTTGTCTG      1020

CTGCAGCATC GTTCTGTGTT GTCTCTGTCT GACTGTGTTT CTGTATTTGT CTGAAAATTA      1080

GGGCCAGACT GTTACCACTC CCTTAAGTTT GACCTTAGGT CACTGGAAAG ATGTCGAGCG      1140

GATCGCTCAC AACCAGTCGG TAGATGTCAA GAAGAGACGT TGGGTTACCT TCTGCTCTGC      1200

AGAATGGCCA ACCTTTACGT CGGATGGCCG CGAGACGGCA CCTTTAACCG AGACCTCATC      1260

ACCCAGGTTA AGATCAAGGT CTTTTCACCT GGCCCGCATG GACACCCAGA CCAGGTCCCC      1320

TACATCGTGA CCTGGGAAGC CTTGGCTTTT GACCCCCCTC CCTGGGTCAA GCCCTTTGTA      1380

CACCCTAAGC CTCCGCCTCC TCTTCCTCCA TCCGCCCCGT CTCTCCCCCT TGAACCTCCT      1440

CGTTCGACCC CGCCTCGATC CTCCCTTTAT CCAGCCCTCA CTCCTTCTCT AGGCGGGAAT      1500

TCGTTAACTC GACCCGCGGG TCGACTCGCG AAGATCTTTC CGCAGCAGCC GCCACCATGG      1560
```

-continued

```
TTACGGATTC GGATCCCGTC GTTTTACAAC GTCGTGACTG GGAAAACCCT GGCGTTACCC     1620

AACTTAATCG CCTTGCAGCA CATCCCCCTT TCGCCAGCTG GCGTAATAGC GAAGAGGCCC     1680

GCACCGATCG CCCTTCCCAA CAGTTGCGCA GCCTGAATGG CGAATGGCGC TTTGCCTGGT     1740

TTCCGGCACC AGAAGCGGTG CCGGAAAGCT GGCTGGAGTG CGATCTTCCT GAGGCCGATA     1800

CTGTCGTCGT CCCCTCAAAC TGGCAGATGC ACGGTTACGA TGCGCCCATC TACACCAACG     1860

TAACCTATCC CATTACGGTC AATCCGCCGT TTGTTCCCAC GGAGAATCCG ACGGGTTGTT     1920

ACTCGCTCAC ATTTAATGTT GATGAAAGCT GGCTACAGGA AGGCCAGACG CGAATTATTT     1980

TTGATGGCGT TAACTCGGCG TTTCATCTGT GGTGCAACGG GCGCTGGGTC GGTTACGGCC     2040

AGGACAGTCG TTTGCCGTCT GAATTTGACC TGAGCGCATT TTTACGCGCC GGAGAAAACC     2100

GCCTCGCGGT GATGGTGCTG CGTTGGAGTG ACGGCAGTTA TCTGGAAGAT CAGGATATGT     2160

GGCGGATGAG CGGCATTTTC CGTGACGTCT CGTTGCTGCA TAAACCGACT ACACAAATCA     2220

GCGATTTCCA TGTTGCCACT CGCTTTAATG ATGATTTCAG CCGCGCTGTA CTGGAGGCTG     2280

AAGTTCAGAT GTGCGGCGAG TTGCGTGACT ACCTACGGGT AACAGTTTCT TTATGGCAGG     2340

GTGAAACGCA GGTCGCCAGC GGCACCGCGC CTTTCGGCGG TGAAATTATC GATGAGCGTG     2400

GTGGTTATGC CGATCGCGTC ACACTACGTC TGAACGTCGA AAACCCGAAA CTGTGGAGCG     2460

CCGAAATCCC GAATCTCTAT CGTGCGGTGG TTGAACTGCA CACCGCCGAC GGCACGCTGA     2520

TTGAAGCAGA AGCCTGCGAT GTCGGTTTCC GCGAGGTGCG GATTGAAAAT GGTCTGCTGC     2580

TGCTGAACGG CAAGCCGTTG CTGATTCGAG GCGTTAACCG TCACGAGCAT CATCCTCTGC     2640

ATGGTCAGGT CATGGATGAG CAGACGATGG TGCAGGATAT CCTGCTGATG AAGCAGAACA     2700

ACTTTAACGC CGTGCGCTGT TCGCATTATC CGAACCATCC GCTGTGGTAC ACGCTGTGCG     2760

ACCGCTACGG CCTGTATGTG GTGGATGAAG CCAATATTGA AACCCACGGC ATGGTGCCAA     2820

TGAATCGTCT GACCGATGAT CCGCGCTGGC TACCGGCGAT GAGCGAACGC GTAACGCGAA     2880

TGGTGCAGCG CGATCGTAAT CACCCGAGTG TGATCATCTG GTCGCTGGGG AATGAATCAG     2940

GCCACGGCGC TAATCACGAC GCGCTGTATC GCTGGATCAA ATCTGTCGAT CCTTCCCGCC     3000

CGGTGCAGTA TGAAGGCGGC GGAGCCGACA CCACGGCCAC CGATATTATT TGCCCGATGT     3060

ACGCGCGCGT GGATGAAGAC CAGCCCTTCC CGGCTGTGCC GAAATGGTCC ATCAAAAAAT     3120

GGCTTTCGCT ACCTGGAGAG ACGCGCCCGC TGATCCTTTG CGAATACGCC CACGCGATGG     3180

GTAACAGTCT TGGCGGTTTC GCTAAATACT GGCAGGCGTT TCGTCAGTAT CCCCGTTTAC     3240

AGGGCGGCTT CGTCTGGGAC TGGGTGGATC AGTCGCTGAT TAAATATGAT GAAAACGGCA     3300

ACCCGTGGTC GGCTTACGGC GGTGATTTTG GCGATACGCC GAACGATCGC CAGTTCTGTA     3360

TGAACGGTCT GGTCTTTGCC GACCGCACGC CGCATCCAGC GCTGACGGAA GCAAAACACC     3420

AGCAGCAGTT TTTCCAGTTC CGTTTATCCG GGCAAACCAT CGAAGTGACC AGCGAATACC     3480

TGTTCCGTCA TAGCGATAAC GAGCTCCTGC ACTGGATGGT GGCGCTGGAT GGTAAGCCGC     3540

TGGCAAGCGG TGAAGTGCCT CTGGATGTCG CTCCACAAGG TAAACAGTTG ATTGAACTGC     3600

CTGAACTACC GCAGCCGGAG AGCGCCGGGC AACTCTGGCT CACAGTACGC GTAGTGCAAC     3660

CGAACGCGAC CGCATGGTCA GAAGCCGGGC ACATCAGCGC CTGGCAGCAG TGGCGTCTGG     3720

CGGAAAACCT CAGTGTGACG CTCCCCGCCG CGTCCCACGC CATCCCGCAT CTGACCACCA     3780

GCGAAATGGA TTTTTGCATC GAGCTGGGTA ATAAGCGTTG GCAATTTAAC CGCCAGTCAG     3840

GCTTTCTTTC ACAGATGTGG ATTGGCGATA AAAAACAACT GCTGACGCCG CTGCGCGATC     3900
```

```
AGTTCACCCG TGCACCGCTG GATAACGACA TTGGCGTAAG TGAAGCGACC CGCATTGACC    3960

CTAACGCCTG GGTCGAACGC TGGAAGGCGG CGGGCCATTA CCAGGCCGAA GCAGCGTTGT    4020

TGCAGTGCAC GGCAGATACA CTTGCTGATG CGGTGCTGAT TACGACCGCT CACGCGTGGC    4080

AGCATCAGGG GAAAACCTTA TTTATCAGCC GGAAAACCTA CCGGATTGAT GGTAGTGGTC    4140

AAATGGCGAT TACCGTTGAT GTTGAAGTGG CGAGCGATAC ACCGCATCCG GCGCGGATTG    4200

GCCTGAACTG CCAGCTGGCG CAGGTAGCAG AGCGGGTAAA CTGGCTCGGA TTAGGGCCGC    4260

AAGAAAACTA TCCCGACCGC CTTACTGCCG CCTGTTTTGA CCGCTGGGAT CTGCCATTGT    4320

CAGACATGTA TACCCCGTAC GTCTTCCCGA GCGAAAACGG TCTGCGCTGC GGGACGCGCG    4380

AATTGAATTA TGGCCCACAC CAGTGGCGCG GCGACTTCCA GTTCAACATC AGCCGCTACA    4440

GTCAACAGCA ACTGATGGAA ACCAGCCATC GCCATCTGCT GCACGCGGAA GAAGGCACAT    4500

GGCTGAATAT CGACGGTTTC CATATGGGGA TTGGTGGCGA CGACTCCTGG AGCCCGTCAG    4560

TATCGGCGGA ATTGCAGCTG AGCGCCGGTC GCTACCATTA CCAGTTGGTC TGGTGTCAAA    4620

AATAATAATA ACCGGGCAGG CCATGTCTGC CCGTATTTCG CGTAAGGAAA TCCATTATGT    4680

ACTATTTCTA GAGAATTCCC CCCTCTCCCT CCCCCCCCCC TAACGTTACT GGCCGAAGCC    4740

GCTTGGAATA AGGCCGGTGT GCGTTTGTCT ATATGTTATT TTCCACCATA TTGCCGTCTT    4800

TTGGCAATGT GAGGGCCCGG AAACCTGGCC CTGTCTTCTT GACGAGCATT CCTAGGGGTC    4860

TTTCCCCTCT GCGCAAAGGA ATGCAAGGTC TGTTGAATGT CGTGAAGGAA GCAGTTCCTC    4920

TGGAAGCTTC TTGAAGACAA ACAACGTCTG TAGCGACCCT TTGCAGGCAG CGGAACCCCC    4980

CACCTGGCGA CAGGTGCCTC TGCGGCCAAA AGCCACGTGT ATAAGATACA CCTGCAAAGG    5040

CGGCACAACC CCAGTGCCAC GTTGTGAGTT GGATAGTTGT GGAAAGAGTC AAATGGCTCT    5100

CCTCAAGCGT ATTCAACAAG GGGCTGAAGG ATGCCCAGAA GGTACCCCAT TGTATGGGAT    5160

CTGATCTGGG GCCTCGGTGC ACATGCTTTA CATGTGTTTA GTCGAGGTTA AAAAACGTCT    5220

AGGCCCCCCG AACCACGGGG ACGTGGTTTT CCTTTGAAAA ACACGATGAT AATATGGCCA    5280

AGCTCCTAGG CTTTTGCAAA AAGCTCCCGG GAGCTTGGAT ATCCATTTTC GGATCTGATC    5340

AAGAGACAGG ATGAGGATCG TTTCGCATGA TTGAACAAGA TGGATTGCAC GCAGGTTCTC    5400

CGGCCGCTTG GGTGGAGAGG CTATTCGGCT ATGACTGGGC ACAACAGACA ATCGGCTGCT    5460

CTGATGCCGC CGTGTTCCGG CTGTCAGCGC AGGGGCGCCC GGTTCTTTTT GTCAAGACCG    5520

ACCTGTCCGG TGCCCTGAAT GAACTGCAGG ACGAGGCAGC GCGGCTATCG TGGCTGGCCA    5580

CGACGGGCGT TCCTTGCGCA GCTGTGCTCG ACGTTGTCAC TGAAGCGGGA AGGGACTGGC    5640

TGCTATTGGG CGAAGTGCCG GGGCAGGATC TCCTGTCATC TCACCTTGCT CCTGCCGAGA    5700

AAGTATCCAT CATGGCTGAT GCAATGCGGC GGCTGCATAC GCTTGATCCG GCTACCTGCC    5760

CATTCGACCA CCAAGCGAAA CATCGCATCG AGCGAGCACG TACTCGGATG AAGCCGGTC     5820

TTGTCGATCA GGATGATCTG GACGAAGAGC ATCAGGGGCT CGCGCCAGCC GAACTGTTCG    5880

CCAGGCTCAA GGCGCGCATG CCCGACGGCG AGGATCTCGT CGTGACCCAT GGCGATGCCT    5940

GCTTGCCGAA TATCATGGTG GAAAATGGCC GCTTTTCTGG ATTCATCGAC TGTGGCCGGC    6000

TGGGTGTGGC GGACCGCTAT CAGGACATAG CGTTGGCTAC CCGTGATATT GCTGAAGAGC    6060

TTGGCGGCGA ATGGGCTGAC CGCTTCCTCG TGCTTTACGG TATCGCCGCT CCCGATTCGC    6120

AGCGCATCGC CTTCTATCGC CTTCTTGACG AGTTCTTCTG AGCGGGACTC TGGGGTTCGC    6180

CTTGACTTGC TGTTTCTAAA AGAAGGTGGC CTCTGTGCGG CCCTAAAGGA AGAGTGCTGT    6240

TTTTACATAG ACCACTCAGG TGCAGTACGG GACTCCATGA AAAAACTCAA AGAAAAACTG    6300
```

-continued

```
GATAAAAGAC AGTTAGAGCG CCAGAAAAGC CAAAACTGGT ATGAAGGATG GTTCAATAAC    6360

TCCCCTTGGT TCACTACCCT GCTATCAACC ATCGCTGGGC CCCTATTACT CCTCCTTCTG    6420

TTGCTCATCC TCGGGCCATG CATAGGGAAG GTGCCTCTTA CCCATCAACA TCTTTGCAAC    6480

CAGACCTTAC CCATCAATTC CTCTAAAAAC CATCAGTATC TGCTCCCCTC AAACCATAGC    6540

TGGTGGGCCT GCAGCACTGG CCTCACCCCC TGCCTCTCCA CCTCAGTTTT TAATCAGTCT    6600

AAAGACTTCT GTGTCCAGGT CCAGCTGATC CCCCGCATCT ATTACCATTC TGAAGAAACC    6660

TTGTTACAAG CCTATGACAA ATCACCCCCC AGGTTTAAAA GAGAGCCTGC CTCACTTACC    6720

CTAGCTGTCT TCCTGGGGTT AGGGATTGCG GCAGGTATAG GTACTGGCTC AACCGCCCTA    6780

ATTAAAGGGC CCATAGACCT TCAGCAAGGC CTAACCAGCC TCCAAATCGC CATTGACGCT    6840

GACCTCCGGG CCCTTCAGGA CTCAATCAGC AAGCTAGAGG ACTCACTGAC TTCCCTATCT    6900

GAGGTAGTAC TCCAAAATAG GAGAGGCCTT GACTTACTAT TCCTTAAAGA AGGAGGCCTC    6960

TGCGCGGCCC TAAAAGAAGA GTGCTGTTTT TATGTAGACC ACTCAGGTGC AGTACGAGAC    7020

TCCATGAAAA AACTTAAAGA AAGACTAGAT AAAAGACAGT TAGAGCGCCA GAAAAACCAA    7080

AACTGGTATG AAGGGTGGTT CAATAACTCC CCTTGGTTTA CTACCCTACT ATCAACCATC    7140

GCTGGGCCCC TATTGCTCCT CCTTTTGTTA CTCACTCTTG GGCCCTGCAT CATCAATAAA    7200

TTAATCCAAT TCATCAATGA TAGGATAAGT GCAGTCAAAA TTTTAGTCCT TAGACAGAAA    7260

TATCAGACCC TAGATAACGA GGAAAACCTT TAATTTCGCT CTAAGATTAG AGCTATCCAC    7320

AAGAGAAATG GGGGAATGAA AGAAGTGTTT TTCAAGTTAG CTGCAGTAAC GCCATTCATA    7380

AGGCACGCCC AAAGCATAAA GGTTAAAGAA GAAAAAAACC GGGCCAAACA GGATATCTGT    7440

GGTCATACAC CTGGAACCCG GCCCAGGGCC AAACACAGAT GGTTCCCAGA AATAAAATGA    7500

GTCAACAGCA GTTTCCAGGG TGCCCCTCAA CTGTTTCAAG AAACTCCCAT GACCGGAGCT    7560

CACCCCTGAC TTATTTGAAC TAACCAATCA CCTTGCTTCT CGCTTCTGTA CCCGCGCTTT    7620

TTGCTATAAA AGGAGCTCAG AAATTCCACT CGGCGCGCCA GTCTTCCAAG AGACTGAGTC    7680

GCCCGGGTAC CCGTGTGATC AATAAAACCT CTTGCTACTT GCATCCGAAG TCGTGGTCTC    7740

GCTGTTCCTT GGGAAGGTCT CCCCTAATTG ATTGACCGCC CGGACTGGGG GTCTCTCATT    7800

GGAATTCATC GATGATATCA GCCAATTCGC CCTATAGTGA GTCGTATTAC AATTCACTGG    7860

CCGTCGTTTT ACAACGTCGT GACTGGGAAA ACCCTGGCGT TACCCAACTT AATCGCCTTG    7920

CAGCACATCC CCCTTTCGCC AGCTGGCGTA ATAGCGAAGA GGCCCGCACC GATCGCCCTT    7980

CCCAACAGTT GCGCAGCCTG AATGGCGAAT GGAAATTGTA AACGTTAATA TTTTGTTAAA    8040

ATTCGCGTTA AATATTTGTT AAATCAGCTC ATTTTTTAAC CAATAGGCCG AAATCGGCAA    8100

AATCCCTTAT AAATCAAAAG AATAGACCGA GATAGGGTTG AGTGTTGTTC CAGTTTGGAA    8160

CAAGAGTCCA CTATTAAAGA ACGTGGACTC CAACGTCAAA GGGCGAAAAA CCGTCTATCA    8220

GGGCGATGGC CCACTACGTG AACCATCACC CAAATCAAGT TTTTTGCGGT CGAGGTGCCG    8280

TAAAGCTCTA AATCGGAACC CTAAAGGGAG CCCCCGATTT AGAGCTTGAC GGGGAAAGCC    8340

GGCGAACGTG GCGAGAAAGG AAGGGAAGAA AGCGAAAGGA GCGGGCGCTA GGGCGCTGGC    8400

AAGTGTAGCG GTCACGCTGC GCGTAACCAC CACACCCGCC GCGCTTAATG CGCCGCTACA    8460

GGGCGCGTCG CCTGATGCGG TATTTTCTCC TTACGCATCT GTGCGGTATT TCACACCGCA    8520

TATGGTGCAC TCTCAGTACA ATCTGCTCTG ATGCCGCATA GTTAAGCCAG CCCCGACACC    8580

CGCCAACACC CGCTGACGCG CCCTGACGGG CTTGTCTGCT CCCGGCATCC GCTTACAGAC    8640
```

```
AAGCTGTGAC CGTCTCCGGG AGCTGCATGT GTCAGAGGTT TTCACCGTCA TCACCGAAAC    8700

GCGCGAGACG AAAGGGCCTC GTGATACGCC TATTTTTATA GGTTAATGTC ATGATAATAA    8760

TGGTTTCTTA GACGTCAGGT GGCACTTTTC GGGGAAATGT GCGCGGAACC CCTATTTGTT    8820

TATTTTTCTA AATACATTCA AATATGTATC CGCTCATGAG ACAATAACCC TGATAAATGC    8880

TTCAATAATA TTGAAAAAGG AAGAGTATGA GTATTCAACA TTTCCGTGTC GCCCTTATTC    8940

CCTTTTTTGC GGCATTTTGC CTTCCTGTTT TTGCTCACCC AGAAACGCTG GTGAAAGTAA    9000

AAGATGCTGA AGATCAGTTG GGTGCACGAG TGGGTTACAT CGAACTGGAT CTCAACAGCG    9060

GTAAGATCCT TGAGAGTTTT CGCCCCGAAG AACGTTTTCC AATGATGAGC ACTTTTAAAG    9120

TTCTGCTATG TCATACACTA TTATCCCGTA TTGACGCCGG GCAAGAGCAA CTCGGTCGCC    9180

GGGCGCGGTA TTCTCAGAAT GACTTGGTTG AGTACTCACC AGTCACAGAA AAGCATCTTA    9240

CGGATGGCAT GACAGTAAGA GAATTATGCA GTGCTGCCAT AACCATGAGT GATAACACTG    9300

CGGCCAACTT ACTTCTGACA ACGATCGGAG GACCGAAGGA GCTAACCGCT TTTTTGCACA    9360

ACATGGGGGA TCATGTAACT CGCCTTGATC GTTGGGAACC GGAGCTGAAT GAAGCCATAC    9420

CAAACGACGA GCGTGACACC ACGATGCCTG TAGCAATGCC AACAACGTTG CGCAAACTAT    9480

TAACTGGCGA ACTACTTACT CTAGCTTCCC GGCAACAATT AATAGACTGG ATGGAGGCGG    9540

ATAAAGTTGC AGGACCACTT CTGCGCTCGG CCCTTCCGGC TGGCTGGTTT ATTGCTGATA    9600

AATCTGGAGC CGGTGAGCGT GGGTCTCGCG GTATCATTGC AGCACTGGGG CCAGATGGTA    9660

AGCCCTCCCG TATCGTAGTT ATCTACACGA CGGGGAGTCA GGCAACTATG GATGAACGAA    9720

ATAGACAGAT CGCTGAGATA GGTGCCTCAC TGATTAAGCA TTGGTAACTG TCAGACCAAG    9780

TTTACTCATA TATACTTTAG ATTGATTTAA AACTTCATTT TTAATTTAAA AGGATCTAGG    9840

TGAAGATCCT TTTTGATAAT CTCATGACCA AAATCCCTTA ACGTGAGTTT TCGTTCCACT    9900

GAGCGTCAGA CCCCGTAGAA AAGATCAAAG GATCTTCTTG AGATCCTTTT TTTCTGCGCG    9960

TAATCTGCTG CTTGCAAACA AAAAAACCAC CGCTACCAGC GGTGGTTTGT TGCCGGATC    10020

AAGAGCTACC AACTCTTTTT CCGAAGGTAA CTGGCTTCAG CAGAGCGCAG ATACCAAATA    10080

CTGTCCTTCT AGTGTAGCCG TAGTTAGGCC ACCACTTCAA GAACTCTGTA GCACCGCCTA    10140

CATACCTCGC TCTGCTAATC CTGTTACCAG TGGCTGCTGC CAGTGGCGAT AAGTCGTGTC    10200

TTACCGGGTT GGACTCAAGA CGATAGTTAC CGGATAAGGC GCAGCGGTCG GGCTGAACGG    10260

GGGGTTCGTG CACACAGCCC AGCTTGGAGC GAACGACCTA CACCGAACTG AGATACCTAC    10320

AGCGTGAGCT ATGAGAAAGC GCCACGCTTC CCGAAGGGAG AAAGGCGGAC AGGTATCCGG    10380

TAAGCGGCAG GGTCGGAACA GGAGAGCGCA CGAGGGAGCT TCCAGGGGGA AACGCCTGGT    10440

ATCTTTATAG TCCTGTCGGG TTTCGCCACC TCTGACTTGA GCGTCGATTT TTGTGATGCT    10500

CGTCAGGGGG GCGGAGCCTA TCGAAAAACG CCAGCAACGC GGCCTTTTTA CGGTTCCTGG    10560

CCTTTTGCTG GCCTTTTGCT CACATGTTCT TTCCTGCGTT ATCCCCTGAT TCTGTGGATA    10620

ACCGTATTAC CGCCTTTGAG TGAGCTGATA CCGCTCGCCG CAGCCGAACG ACCGAGCGCA    10680

GCGAGTCAGT GAGCGAGGAA GCGGAAGAGC GCCCAATACG CAAACCGCCT CTCCCCGCGC    10740

GTTGGCCGAT TCATTAATGC AGCTGGCACG ACAGGTTTCC CGACTGGAAA GCGGGCAGTG    10800

AGCGCAACGC AATTAATGTG AGTTAGCTCA CTCATTAGGC ACCCCAGGCT TTACACTTTA    10860

TGCTTCCGGC TCGTATGTTG TGTGGAATTG TGAGCGGATA ACAATTTCAC ACAGGAAACA    10920

GCTATGACCA TGATTACGCC AAGCTATTTA GGTGACACTA TAGAATACTC              10970
```